US012674784B2

(12) United States Patent (10) Patent No.: US 12,674,784 B2

Schaubmar et al. (45) Date of Patent: Jul. 7, 2026

(54) CATION CHROMATOGRAPHY USING PREDICTED ELUTION BUFFER SALT CONCENTRATION

(71) Applicant: HOFFMANN-LA ROCHE INC., Little Falls, NJ (US)

(72) Inventors: Andreas Schaubmar, Penzberg (DE); Felix Wittkopp, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 919 days.

(21) Appl. No.: 17/675,193

(22) Filed: Feb. 18, 2022

(65) Prior Publication Data

US 2022/0187256 A1 Jun. 16, 2022

Related U.S. Application Data

(63) Continuation of application No. PCT/EP2020/025433, filed on Sep. 24, 2020.

(30) Foreign Application Priority Data

Sep. 25, 2019 (EP) .................................... 19199438

(51) Int. Cl.
| | |
|---|---|
| *G01N 30/64* | (2006.01) |
| *C07K 1/18* | (2006.01) |

(Continued)

(52) U.S. Cl.
CPC .............. *G01N 30/64* (2013.01); *C07K 1/18* (2013.01); *G01N 2030/027* (2013.01); *G01N 2030/067* (2013.01)

(58) Field of Classification Search
CPC ........ C07K 1/16; C07K 1/18; G01N 30/8658; G01N 30/8696; G01N 30/8693

(Continued)

(56) References Cited

U.S. PATENT DOCUMENTS

| | | | |
|---|---|---|---|
| 2007/0167612 A1 | 7/2007 | Hua Zhou | |
| 2017/0065906 A1 | 3/2017 | Oroskar et al. | |
| 2018/0143117 A1 | 5/2018 | He | |

FOREIGN PATENT DOCUMENTS

| | | |
|---|---|---|
| CN | 101918430 A | 12/2010 |
| CN | 102574911 A | 7/2012 |

(Continued)

OTHER PUBLICATIONS

International Search Report PCT/ISA/210 and Written Opinion PCT/ISA/237 for PCT/EP2020/025433 dated Sep. 24, 2020.

(Continued)

*Primary Examiner* — Claire A Norris

(74) *Attorney, Agent, or Firm* — Harness, Dickey & Pierce, P.L.C.

(57) ABSTRACT

The invention relates to a chromatography method of producing a target elution volume comprising a first and a second target protein. The method includes providing a cation exchange chromatography column; applying a protein solution on the column, the protein solution comprising the first target protein, a second target protein and optionally one or more further proteins; inputting an optimization criterion; computing chromatography simulations for computing an elution buffer salt concentration adapted to provide a target elution volume matching the optimization criterion best; computing the pooling borders of the target elution volume as a function of at least the computed salt concentration and the input optimization criterion; applying an elution buffer having the computed salt concentration on the chromatography column; performing the elution; and collecting the computed target elution volume.

26 Claims, 17 Drawing Sheets

Specification includes a Sequence Listing.

(51) Int. Cl.
　　G01N 30/02　　　(2006.01)
　　G01N 30/06　　　(2006.01)
(58) Field of Classification Search
　　USPC .......................... 210/198.2, 143, 656; 703/2
　　See application file for complete search history.

(56)　　　　　　　References Cited

FOREIGN PATENT DOCUMENTS

| | | | | |
|---|---|---|---|---|
| GB | 2539420 A | * | 12/2016 | .......... B01D 15/166 |
| JP | H08503714 A | | 4/1996 | |
| WO | 94/03603 A1 | | 2/1994 | |
| WO | 00/53730 A2 | | 9/2000 | |
| WO | WO-2017/055540 A1 | | 4/2017 | |

OTHER PUBLICATIONS

Huuk Thiemo C et al., "Model-Based Integrated Optimization and Evaluation of a Multi-Step Ion Exchange Chromatography", Elsevier Science, Amsterdam, NL, vol. 136, Sep. 19, 2014.

Borg Niklas et al., "Modeling and Robust Pooling Design of a Preparative Cation-Exchange Chromatography Step for Purification of Monoclonal Antibody Monomer from Aggregates", Journal of Chromatography A, Elsevier, Amersterdam, NL, vol. 1359, Jul. 21, 2014.

Anton Sellberg et al., "Model-Based Comparison of Antibody Dimerization in Continuous and Batch-Wise Downstream Processing", Antibodies, vol. 4, No. 3, Jul. 10, 2015.

Felix Wittkopp et al., "Modeling and Simulation of Protein Elution in Linear pH and Salt Gradients on Weak, Strong, and Mixed Cation Exchange Resins Applying an Extended Donnan Ion Exchange Model" Journal of Chromatography A, vol. 1545, Apr. 1, 2018.

Simon Kluters et al., "Application of Linear pH Gradients for the Modeling of Ion Exchange Chromatography: Separation of Monoclonal Antibody Monomer from Aggregates: Liquid Chromatography", Journal of Separation Science., vol. 39, No. 4, Dec. 15, 2015.

Andreas Seidel-Morgenstern et al, "Modeling and Model Parameters: Schmidt-T: PREP.CHROM. 2ED 0-BK" Sep. 27, 2012.

Jakobsson N et al., "Using Computer Simulation to Assist in the Robustness Analysis of an Ion-Exchange Chromatography Step", Journal of Chromatography A, Elsevier, Amsterdam, NL, vol. 1063, No. 1-2, Jan. 21, 2005.

C.A. Orellana et al., "Mathematical Modeling of Elution Curves for a Protein Mixture in Ion Exchange Chromatography applied to High Protein Concentration", Biotechnology and Bioengineering, vol. 104, No. 3, Oct. 15, 2009.

Novic M et al., "Computer Simulation of Ion Chromatography Separation: An Algorithm Enabling Continuous Monitoring of Anion Distribution of an Ion-Exchange Chromatography Column", Journal of Chromatography A, Elsevier, Amsterdam, NL, vol. 922, No. 1-2, Jul. 13, 2001.

International Search Report and Written Opinion for PCT/EP2020/025433 dated Mar. 4, 2021.

Search Report for European Application No. 20 786 452.1 dated Sep. 15, 2023.

Search Report for European Application No. 19 199 438.3 dated Mar. 3, 2020.

Search Report for Singapore Application No. 11202201472S dated Aug. 1, 2023.

Notice of Reasons for Rejection for Japanese Application No. 2022-515644.

Second Notice of Reasons for Rejection for Japanese Application No. 2022-515644.

Office Action for Canadian Application No. 3,148,467 dated Mar. 14, 2024.

Office Action for Brazilian Application No. BR112022003710-4 dated Mar. 12, 2024.

Kluters et al., "Application of linear pH gradients for the modeling of ion exchange chromatography: separation of monoclonal antibody monomer", J Sep Sci, Feb. 2016, 93(4), 663-675.

Huuk et el., "Modeling of Complex Antibodies Elution Behavior under High Protein Load Desities in Ion Exchange Chromatography Using an Asymmetric Activity Coefficient," Biotechnol. J., 12: 1600336. doi:10.1002/biot.201600336, 2017.

Müller-Späth T, Ströhlein G, Aumann L, et al. in "Model simulation and experimental verification of a cation-exchange IgG capture step in batch and continuous chromatography", J Chromatogr A. 2011;1218(31):5195-5204, doi:10.1016.

T. Hahn, T. Huuk, V. Heuveline, J. Hubbuch, Simulating and Optimizing Preparative Protein Chromatography with ChromX, Journal of Chemical Education, 92 (2015) 1497-1502).

M. Schmidt, M. Hafner, C. Frech, Modeling of salt and pH gradient elution in ion-exchange chromatography, Journal of Separation Science, 37 (2014) 5-13).

T. Ishihara, T. Kadoya, H. Yoshida, T. Tamada, S. Yamamoto, Rational methods for predicting human monoclonal antibodies retention in protein A affinity chromatography and cation exchange chromatography: Structure-based chromatography design for monoclonal antibodies, Journal of Chromatography A, 1093 (2005) 126-138).

Office Action dated Apr. 15, 2023, issued in corresponding Chinese Patent Application No. 202080062940.7.

International Preliminary Report on Patentability for PCT/EP2020/025433 dated Apr. 7, 2022.

Office Action dated Nov. 10, 2025 issued in European patent application No. 20786452.1.

Nooshafarin Sanaie et al: "Applying high-throughput methods to develop a purification process for a highly glycosylated protein", Biotechnology Journal, Wiley-VCH Verlag, Weinheim, DE, vol. 7, No. 10, Sep. 24, 2012 (Sep. 24, 2012), pp. 1242-1255, XP072399243.

* cited by examiner

Selecting the Model(s)

400

Column model (according to Schmidt Traub et al. „Preparative Chromatography" 2012, Wiley-VCH)

Transport Dispersive $$\frac{\delta c}{\delta t}(x,t) = -\frac{\upsilon(t)}{\varepsilon_{col}}\frac{\delta c}{\delta x}(x,t) + D_{ax}\frac{\delta^2 c}{\delta x^2}(x,t) - \frac{1-\varepsilon_{col}}{\varepsilon_{col}}\left(\varepsilon_{part}\frac{\delta c}{\delta t} + (1-\varepsilon_{part})\frac{\delta q}{\delta t}(x,t)\right)$$

Pore model (according to Schmidt Traub et al. „Preparative Chromatography" 2012, Wiley-VCH)

Lumped Rate Model $$\frac{\delta c_p}{\delta t}(x,t) = \frac{3}{\tau_{part}}\frac{k_{eff}}{\varepsilon_{part}}(c(x,t) - c_p(x,t)) - \frac{1-\varepsilon_{part}}{\varepsilon_{part}}\frac{\delta q}{\delta t}(x,t)$$

Isotherm (according to Kluters et al., "Application of linear pH gradients for the modeling of ion exchange chromatography: Separation of monoclonal antibody monomer from aggregates", J Sep Sci. 2016 Feb; 39(4):663-75.):

$$\frac{\delta_{q_i}}{\delta t} = k_{kin,i} = \exp(Gp_i + v_i Gs) \, q_{salt}^{-v_i} \cdot C_{p,i}^{-q_i} \cdot C_{p,salt}^{v_i}$$

$$\text{with } v_i = \frac{-N_{Car}}{1+10^{pKa_{Car}-pH}} + \frac{N_{Ami}}{1+10^{pH-pKa_{Ami}}} + \frac{N_{His}}{1+10^{pH-pKa_{His}}} + \frac{N_{NTerm}}{1+10^{pH-pKa_{NTerm}}}$$

ph-dependent ION Exchange isotherm (IEC 2015) by Kluters et al.

Fig. 4C

Entering Parameters (Model, Column, etc.)

Entering Parameters (Protein 1, Protein 2, .... )

Obtaining a Target Protein P1
(from a solution comprising P1, P2 and P3)

Identification of optimal salt concentration

| Iteration | Salt Stufe Concentration | Purity Protein 1 | Yield Protein 1 | Objective $\hat{e}$ |
|---|---|---|---|---|
| 23 | 0.345893 | 0.738685 | 0.862189 | 2.49157 |
| 18 | 0.346202 | 0.737446 | 0.864401 | 2.49163 |
| 1 | 0.34821 | 0.729292 | 0.878208 | 2.49298 |
| 10 | 0.342544 | 0.751832 | 0.836734 | 2.49335 |
| 11 | 0.349595 | 0.732567 | 0.887164 | 2.49488 |
| 2 | 0.349958 | 0.722053 | 0.889435 | 2.4955 |
| 22 | 0.338399 | 0.767359 | 0.801499 | 2.50167 |
| 17 | 0.353815 | 0.705651 | 0.911636 | 2.5055 |

Results 510

Identification of optimal salt concentration

X: [Iteration ▼]    Y: [Objective ▼]    Z: [None ▼]

Identification of optimal salt concentration

| Results | | | | | 617 |
|---|---|---|---|---|---|
| Iteration | Salt Step Concentration | Purity Protein 1 | Purity Protein 2 | Reference Compar. | Objective |
| 35 | 0.388547 | 0.55022 | 0.449492 | 0.000553859 | 0.000553859 |
| 36 | 0.392303 | 0.535252 | 0.464414 | 0.0206218 | 0.0206218 |
| 37 | 0.389568 | 0.546074 | 0.453626 | 0.00534392 | 0.00534392 |
| 38 | 0.393545 | 0.53048 | 0.469168 | 0.0273574 | 0.0273574 |
| 39 | 0.389494 | 0.546373 | 0.453328 | 0.00492257 | 0.00492257 |
| 40 | 0.389293 | 0.547186 | 0.452518 | 0.00377636 | 0.00377636 |
| 41 | 0.392007 | 0.536403 | 0.463267 | 0.0189974 | 0.0189974 |
| 42 | 0.39018 | 0.543616 | 0.456077 | 0.00881355 | 0.00881355 |

Identification of optimal salt concentration

| Elution | Load [g/L] | Column Length [cm] | Column Volume [ml] | Pooling | Pool content 2x gly. [%] Protein P1 | | Pool content 1x gly. [%] Protein P2 | |
|---|---|---|---|---|---|---|---|---|
| | | | | | Experiment | Model | Experiment | Model |
| CF200 Cycle 1 | 40 % B | 45 | 22.5 | 11.000 | 0.5 OD→6 CV | 56 | 51 | 44 | 49 |
| | | | | → fit ionic capacity from 670 to 690 mol/L (+3%) (PorosXS specification: ± 13%) | | 56 | 56 √ | 44 | 44 √ |

Protein P1          Protein P2          Protein P3

CATION CHROMATOGRAPHY USING PREDICTED ELUTION BUFFER SALT CONCENTRATION

CROSS-REFERENCE TO RELATED APPLICATIONS

This application is a PCT Bypass Continuation under 35 U.S.C. § 371 of PCT International Application No. PCT/EP2020/025433 which has an International filing date of Sep. 24, 2020, which claims priority to EP Application No. 19199438.3, filed Sep. 25, 2019, the entire contents of each of which are hereby incorporated by reference.

INCORPORATION BY REFERENCE OF SEQUENCE LISTING

This application contains references to amino acid sequences and/or nucleic acid sequences which have been submitted herewith as the sequence listing text file entitled "000016us_SequenceListing_ST25.txt", file size 16,316 bytes, created on 14 Jul. 2025. The aforementioned sequence listing is hereby incorporated by reference in its entirety pursuant to 37 C.F.R. § 1.52(e).

FIELD OF THE INVENTION

The invention relates to the field of chromatography, and more particular to the field of cation chromatography for obtaining specific proteins.

BACKGROUND AND RELATED ART

Cation exchange chromatography is a form of ion exchange chromatography commonly used to separate molecules based on their net surface charge. A negatively charged ion exchange resin with an affinity for molecules (e.g. proteins or peptides) having net positive surface charges is used both for preparative and analytical purposes.

A protein's net surface charge changes with pH in a manner that is dictated by a protein's isoelectric point ("pI"). Proteins with different pI values will have different degrees of charge at a given pH and thereby have different affinities for the negatively charged surface groups on the particles of the ion exchange medium in the chromatography column. Therefore, proteins with different pI values will bind to the chromatography resin with different strengths, facilitating their separation.

However, not all proteins and peptides that need to be separated have sufficiently different pI values to allow for a clear separation in a chromatography column. Furthermore, the separation may in addition depend on the number of amino acid side residues interacting with the column: due to steric factors, not all charged groups of a protein can participate in the binding. In particular, the resolution of protein glycoforms and proteins comprising other types of posttranslational modifications (PTMs) in a chromatography column is a challenge.

Glycosylation is one of the most common posttranslational modifications (PTMs) of proteins. Glycosylation involves the covalent attachment of oligosaccharides (glycans) to the amino acid backbone of a protein, in particular to serine/threonine (O-glycosylation) or asparagine (N-glycosylation) amino acid residues. The glycan residues have a major impact on the biological function of the protein as they may affect protein stability, solubility, antigenicity, folding and serum half-life. Protein glycosylation and many other forms of PTMs (e.g. phosphorylation, methylation, succinimidation, oxidation, N-terminal methionine-loss and others) are created in complex processes that involve various enzymes and substrates, and depend on the host organism, production cell line, and culture conditions.

Glycosylation and other types of PTMs are critical quality attributes of therapeutic proteins. PTMs through conformational changes can modulate therapeutic value (potency) of proteins and peptides e.g. complement dependent cell cytotoxicity (CDCC) and antibody-dependent cell cytotoxicity (ADCC) activities of MAbs.

Hence, the problems of current chromatography techniques used for separating protein variants subjected to glycosylation and/or other forms of PTMs is a severe problem when it comes to selectively eluting a protein having a particular PTM or when it comes to obtaining an elution comprising a desired ratio of two or more protein variants differing from each other only in respect to the type, number and/or position of PTMs.

SUMMARY

It is an objective of the present invention to provide for a method for obtaining a target elution volume comprising two or more target proteins using ion exchange chromatography and a corresponding chromatography control system as specified in the independent claims. Embodiments of the invention are given in the dependent claims. Embodiments of the present invention can be freely combined with each other if they are not mutually exclusive.

In one aspect, the invention relates to a chromatography method of producing a target elution volume that comprises a first and a second target protein. The method comprises:

providing a cation exchange chromatography column;

applying a protein solution on the column; the protein solution comprises at least the first target protein, the second target protein and optionally one or more further proteins;

inputting an optimization criterion into the chromatography simulation software; the optimization criterion is a desired property of the target elution volume in respect to the first and second target proteins comprised in the target elution volume; for example, the optimization criterion can be a quantitative property and/or a qualitative property of the two or more target proteins comprised in an elution volume; the quantitate property can be, for example, absolute amounts of the target proteins in an elution volume (e.g. concentrations) or relative amounts (e.g. ratios) of the two or more target proteins; in addition, or alternatively, the criterion can be or comprise one or more qualitative properties, e.g. the purity of one or of both of the target proteins; the optimization criterion can also be a derivative score value computed as a function of one or more qualitative and one or more quantitative properties of the two target proteins.

The chromatography simulation software is configured to compute an elution buffer salt concentration that is adapted to elute the first and the second target protein from the chromatography column such that a target elution volume can be obtained that matches the optimization criterion best. The computation comprises computing a plurality of chromatography simulations as a function of multiple different elution buffer salt concentrations.

The chromatography simulation software is further configured to compute the pooling borders of the target elution volume as a function of at least the computed salt concentration and the input optimization criterion.

The method further comprises:

applying an elution buffer having the computed salt concentration on the chromatography column;

performing the elution with the applied elution buffer; and collecting the computed target elution volume as a separate fraction using the computed pooling borders.

These features may be advantageous as embodiments of the invention allow obtaining target elution volumes comprising a predefined amount, ratio and/or purity of two or more proteins of interest even though these proteins may have a highly similar pI values and may have overlapping elution profiles under some elution conditions.

Without the intention to be bound to any theory, applicant assumes this effect is achieved because the salt concentration of the elution buffer is not a one-fits-all elution salt concentration. Rather, the salt concentration is a concentration that is computationally predicted specifically for the desired optimization criterion, in particular the absolute or relative amount and/or purity of two or more target proteins of interest. This may allow avoiding additional process steps for removing or reducing the amount of particular target proteins in an eluate and/or avoiding additional process steps of concentrating a particular target protein of interest in order to re-combine two or more separately eluted target proteins in a desired ratio.

Applicant has observed that in some pharmaceutical application scenarios, it is desirable to provide drugs consisting of a mixture of two or more target proteins provided in a predefined ratio and/or purity. For example, a drug may consist of a mixture of two PTM-variants of a particular protein P called P1 and P2, whereby the drug is most effective if the variants P1 and P2 are provide in a particular amount ratio. Embodiments of the invention may allow performing the chromatography step that may be performed anyway for extracting and/or up-concentrating specific proteins of interest from the totality of proteins of a cell such that the two or more proteins of interest are readily eluted in the desired ratio, amount and/or purity in a single chromatography run.

The chromatography simulation software may achieve this desirable effect by simulating multiple chromatography runs of the proteins applied on the column for different (hypothetical/candidate) elution buffer salt concentrations for identifying the salt concentration that is optimal for the optimization criterion. This computationally identified salt concentration is then used to create or select the elution buffer to be used for the actual chromatography process such that the salt concentration of the created or selected elution buffer is identical to the computed salt concentration.

The elution buffer obtained by embodiments of the invention is not a "standard"/"one fits all" elution buffer, but is rather an elution buffer specifically adapted to the optimization criterion which may flexibly be defined on a case-by-case basis.

According to embodiments, the optimization criterion is selected from a group comprising:

a) a desired ratio or ratio range of the amounts of the first and of the second target proteins in the target elution volume; in particular, the ratio can be any ratio in a range of 5:95 to 1:1, in particular 1:95 to 1:1;

b) a desired amount or amount range of the first target protein in combination with a desired amount or amount range of the second target protein in the target elution volume; for example, the: amount can be an absolute amount or a concentration;

c) a desired purity or purity range of the first target protein in combination with:

a desired ratio of the amounts of the first and second protein in the target elution volume a desired amount or amount range of the second target protein in the target elution volume;

a desired purity or purity range of the second target protein in the target elution volume;

d) a combination of two or more of the above-mentioned criteria. For example, a complex score computation algorithm may be used to compute a score value for an elution buffer that has a match M1 in respect to a desired target protein ratio and that has a match M2 in respect to a desired purity of the two or more target proteins, whereby M1 has an impact of about 70% on the total score and M2 has an impact of about 30% on the total score. According to another example, the optimization criterion is a combination of a required minimum absolute amount of one or more of the target proteins, a desired ratio range (e.g. 1:2.0 to 1:2.5) and a minimum purity score for one or more of the target proteins.

This may allow a user to identify and use an elution buffer whose salt concentration is optimized for the respective use-case scenario. For example, in a research setting, the protein purity aspect may be less important than in a clinical use case scenario. According to preferred embodiments, the simulation software is configured to generate a GUI enabling a user to enter and/or modify the optimization criterion, e.g. for each individual chromatography run. This may allow to flexibly adapt the chromatography process to different use-case scenarios, different target proteins and target protein combinations and many other factors.

According to embodiments, the applied protein solution comprises the one or more further proteins. The further proteins may have an overlapping elution profile with the target proteins and may contaminate the eluate. By taking into account the purity of the target proteins, in particular the amount and/or chemical properties of the target proteins in the simulations and/or in the computing of the pooling borders, it is possible to identify and use an elution buffer salt concentration which allows to elute the target proteins and the contaminating further proteins such that an acceptable level of purity of the target proteins is achieved.

According to embodiments, the multiple different elution buffer salt concentrations are created automatically, e.g. based on a predefined program routine for creating salt buffer specifications having different salt concentrations but otherwise (e.g. in respect to the pH value) being identical. These automatically created buffer salt concentrations may also be referred to as "hypothetical" or "candidate" elution buffer salt concentrations. For example, the computed salt concentration is the one out of a plurality of candidate elution salt concentrations that has been computationally identified to meet the optimization criterion best. For example, the computing of the elution buffer salt concentration can comprise predicting the amount and/or purity of the one or more target proteins in a target elution volume as a function of a plurality of different candidate elution salt concentrations, and identifying the one of the candidate elution buffer salt concentration that is best suited for collecting a target elution volume comprising the one or more target proteins in the desired amount and/or purity as the elution buffer salt concentration. This identified salt concentration is used as the "computed" elution buffer salt concentration and is used for selecting or creating the elution buffer whose salt concentration is identical to the computed and identified elution buffer salt concentration. This selected or created elution buffer is used for actually performing the elution with the applied elution buffer.

The desired optimization criterion that is input into the chromatography simulation software can be specified, depending on the embodiment, as absolute amounts (e.g. a concentration of each of the target proteins) or a relative amount (e.g. a concentration ratio or a mass ratio of two or more target proteins).

According to embodiments, the method is used for analytical purposes. According to preferred embodiments, the method is used for preparatory purposes.

According to preferred embodiments, the computed salt concentration that is adapted to elute the first target protein is the one out of a plurality of candidate salt concentrations that is suited best for separating the first target protein and/or the second target protein from any one of the further proteins contained in the applied protein solution.

These features may be advantageous as applicant has observed that it is possible to simulate the chromatography process based on a set of known or easily obtainable input data values sufficiently well as to allow to predict a concentration of the salt in the elution buffer that is suitable to elute two or more proteins of interest ("target proteins" such that these target proteins are comprised in a desired amount, ratio and/or purity in a target elution volume. Preferably, the computed salt concentration is best or approximately best suited for separating the first target protein from the further proteins contained in the protein solution.

By eluting the applied protein solution with an elution buffer whose salt concentration corresponds to the predicted suitable or optimal salt concentration, it is possible to perform a high-resolution protein chromatography that is able to separate proteins and protein variants having highly similar chemical properties, including highly similar polarities. Furthermore, the computed elution buffer salt concentration can itself be used as input for performing further predictions, in particular for highly accurately predicting the pooling borders of an elution volume that will comprise the one or more target proteins in the desired amount. The elution buffer salt concentration predicted to be a suitable or optimal salt concentration can be computed as the one out of a plurality of candidate elution salt concentration that is predicted to provide the two or more target proteins in the desired absolute or relative amounts and/or in a desired purity. Accordingly, based on the prediction of the pooling borders as a function of the computationally identified "optimal" elution buffer salt concentration, it is possible to specifically collect the fraction of the total elution volume that comprises the one or more target proteins in the desired amount, ratio and/or purity.

This may be particularly useful when one or more target proteins need to be separated from one or more highly similar other proteins, e.g. from other glycoforms, or if a mixture of two or more highly similar target proteins with a desired ratio (relative amount) shall be obtained.

The method according to embodiments of the invention may have the advantage that highly similar protein variants which could not be separated by cation chromatography previously can now be separated in a single chromatography run: in a first step, a suitable elution buffer salt concentration is predicted and then the elution is performed using an elution buffer having the predicted salt concentration. This may be highly advantageous in any situation where a protein needs to be separated from other, chemically highly similar proteins, or where two or more proteins with highly similar chemical properties need to be obtained in a specific relative amount. For example, the glycosylation pattern of recombinant pharmaceutical proteins often have a strong impact on the quality and efficacy of those proteins. Often, the cell lines used for producing a particular target protein, e.g. an antibody or antibody fragment having a particular glycosylation pattern, do not only produce this particular glycoform, but also one or more other glycoforms including those lacking any glycosylation. By predicting a suitable elution buffer salt concentration first, performing the elution with an elution buffer having the predicted salt concentration and then predicting and collecting the pooling borders, embodiments of the invention may allow specifically one or more glycoforms of interest and obtaining these glycoforms already in a suitable concentration.

Predicting the pooling borders of the target elution volume such that this target elution volume comprises the two or more target proteins in the desired amounts, ratio and/or purity may be beneficial as additional steps for increasing or decreasing the concentration of the target protein(s) can be avoided. This accelerates the process of obtaining one or more target proteins in a desired concentration and also increases the quality of the target proteins as every additional processing step that can be avoided reduces the risk of contaminating or otherwise damaging the target protein(s) contained in the target elution volume.

Embodiments of the invention are particularly suited for separating therapeutic or diagnostic proteins or protein fragments such as antibodies or antibody fragments. Embodiments of the invention may be used for ensuring quality, purity, safety, and efficacy of a biopharmaceutical product by using the chromatography method according to embodiments of the invention for selectively obtaining one or more target proteins in a desired amount.

According to embodiments, the protein solution that is applied on the column is a water based solution comprising one or more salts and one or more proteins.

According to embodiments, the plurality of chromatography simulations are computed as a function of the multiple different elution buffer salt concentrations and as a function of multiple different elution buffer pH values. The computing of the salt concentration comprises computing a combination of the elution buffer salt concentration and of an elution buffer pH value which in combination are adapted to elute the first and the second target proteins from the chromatography column such that a target elution volume can be obtained that matches the optimization criterion best. The chromatography simulations are performed for identifying the combination of the combination of the elution buffer salt concentration and the elution buffer pH value. The pooling borders of the target elution volume are computed as a function of at least the computed combination of the elution buffer salt concentration and the elution buffer pH value and the input optimization criterion. The elution buffer that is applied on the column has the computed salt concentration and the computed pH value.

Applicant has observed that in addition to the salt concentration, also the pH value has a significant impact on the elution profile of different proteins. As the salt concentration, the pH value can easily be set to a particular desired value. The one or more models used for performing the simulations typically take into account both the salt concentration and the pH value of the buffer, to the computation of multiple chromatography runs and/or chromatography elution steps based on a combination of different salt concentrations and different pH values can be performed without the need to adapt the models or implement complex additional program routines. In addition, complex interrelations between the salt concentration and the pH value and their combined impact on the elution profiles can be considered in the simulation process. Furthermore, simulations which are based on the variation of both the salt concentration and the pH value may cover a huge data space and hence have an increased likelihood of identifying a solution buffer that is able to comply with the optimization criterion. For example, if the simulations are performed for 10 different salt concentrations and each salt concentration is simulated based on 10 different pH values, the simulations comprise 10×10=100 different simulations and corresponding theoretical/candidate elution buffer specifications.

According to embodiments, the method comprises automatically or manually selecting or preparing an elution buffer such that the selected or prepared elution buffer has the salt concentration and the pH value which have been identified in the simulations to best meet the optimization criterion. The selected or prepared elution buffer is used as the buffer that is applied on the column to elute the proteins.

Single Target Protein Case Scenario

According to a further use case scenarios described herein, the target elution volume comprises only a single (first) target protein and optionally one or more further (contaminating) proteins. The optimization criterion is a desired absolute amount of the desired target protein and/or a desired purity of the target protein. In particular, the desired amount of the first target protein can be specified in the form of a desired concentration of the first protein in a collected volume of the elution buffer or a derivative value thereof.

For example, in case the desired concentration is provided, the target elution volume can be computed as the elution volume comprising the target protein in the desired concentration, whereby the pooling borders are selected such that the average concentration of the eluted target protein in the target elution volume is identical to the desired concentration. It is possible that during the collection of the target elution volume, the first target protein concentration in the elution buffer leaving the column is higher or lower than the desired concentration.

In case a desired absolute amount is provided, the target elution volume can be computed as the minimum elution volume comprising the first target protein in the desired amount.

Using embodiments of the invention for computing the pooling borders for the target elution volume of a single target protein may be advantageous as it allows collecting the target protein such that the collected target elution volume already comprises the (single) target protein in the desired concentration and/or absolute amount, so additional steps for concentrating or diluting the target protein may be avoided. In addition, applicant has observed that the chromatography method according to embodiments of the invention allows predicting the pooling borders of the target elution volume highly accurately, thereby providing the target protein in a pure, predictable way and minimizing the risk of losing significant parts of the target protein by starting the collection of the elution buffer leaving the column too late or terminating the collection too early.

Multiple Target Proteins Case, General Aspects

According to embodiments, the applied protein solution comprises the first target protein, a second target protein and zero, one or more of the further proteins. The optimization criterion is input into the chromatography simulation software in the form of a relative amount of the first and second target protein, e.g. in the form of a ratio of the first target protein and the second target protein. The chromatography simulation software computes the pooling borders of the target elution volume as a function of at least the computed salt concentration and the input desired ratio. The method is used for producing a target elution volume comprising the desired ratio of the first and second target proteins.

This may be advantageous in particular in use case scenarios where two proteins having highly similar chemical properties, e.g. two glycoforms, shall be separated from all other proteins and shall be obtained in a particular ratio. For example, some glycoforms of biomedically active compounds such as antibodies or antibody fragments have been observed to be particularly effective if two or more different glycoforms are applied in a specific ratio. In state of the art approaches, it was often highly time consuming and sometimes infeasible to obtain a pure protein solution with a defined relative amount of two or more target proteins in cases where these target proteins have highly similar chemical properties. This is because conventional chromatography approaches were not able to separate these proteins from each other. Rather, both proteins were obtained in the elution buffer in a ratio that changes as the elution progresses and that could not be set to a desired value. Embodiments of the invention take advantage of a chromatography simulation software being configured to perform a computation and prediction of the elution behavior of the first target protein, to perform a computation and prediction of the elution behavior of the second target protein (and of any one of the further proteins applied on the columns, if any, at least in case purity of one or more target protein is to be taken into account), and to automatically compute and predict the pooling borders of a target elution volume comprising the first and the second target protein in a desired ratio, amount and/or purity. For example, the concentration of the first and second target protein and optionally also of each of the further proteins comprised in the applied protein solutions, if any, in the elution buffer leaving the column can be predicted for a series of time points (e.g. every second or every minute) in the future both for the first and for the second target protein. The obtained predicted concentration values can be interpolated and/or extrapolated and the absolute and/or relative amount and/or purities of the two or more target proteins for various candidate pooling borders can be obtained. Then, the pooling borders defining a target elution volume comprising the first and the second target protein in the desired amount and/or purity can be output and used for starting and ending the collection of the target elution volume in accordance with the pooling borders.

According to embodiments, the first and the second target proteins are proteins having a low resolution factor, in particular a resolution factor of less than 0.75, and in some examples of less than 0.6 or even of less than 0.5.

The resolution factor as used herein is a numeric value, such as 0.8, 1.0, or 3.0 that is indicative of the degree of peak separation of two types of molecules in the eluate of a chromatography column. In general, resolution is the ability to separate two signals. In terms of chromatography, this is the ability to separate two peaks of two different molecule types. Resolution, R, is given by $$R = \frac{(t_{r2} - t_{r1})}{1/2(w_1 + w_2)},$$

where $t_{r1}$ and $t_{r2}$ and $w_1$ and $w_2$ are the times t and widths w, respectively, of the two immediately adjacent peaks. If the peaks are sufficiently close, which is the pertinent problem, the width w is nearly the same for both peaks. Assuming Gaussian distribution of both types of molecules, a resolution factor of 1 indicates 2.5 percent of the area of the first peak overlaps with the area of the second peak. Similarly, a resolution of 1.5 indicates a difference in retention time of $1.5 \times 4 \times \sigma$, wherein $\sigma$ is the standard deviation of the Gaussian distribution, which corresponds to an overlap of 0.15%. In general, the higher the resolution factor, the better two molecules can be separated. Embodiments of the invention have been observed to be able to separate even proteins having a very low resolution factor, e.g. a resolution factor of less than 0.5.

Embodiments of the invention have been observed to be able to separate proteins even in case they have a very low resolution factor. By taking into account also the chemical nature and the amount of the individual proteins loaded onto a column, by computationally predicting an optimum elution buffer salt concentration specifically for the type and amount of proteins to be applied, and by performing the elution with an elution buffer having the predicted optimum salt concentration, embodiments of the invention have been observed to be able to separate even highly similar proteins from each other and/or to accurately predict a target elution volume comprising one or more target proteins exactly in a desired amount and/or purity.

According to embodiments, the first and the second target proteins are variants of proteins having an identical amino acid sequence but different types, numbers or positions of PTMs. In particular, the first and second target protein are glycoforms.

According to embodiments, the first and the second target proteins are antibody monomers having an identical amino acid sequence and comprising different numbers of glycosyl groups on the FAB fragment.

According to some embodiments, the elution process is a step-wise elution process wherein multiple different elution buffers ("steps") are applied sequentially. In this case, the computational identification of the (most suitable) elution salt concentration, the computation of the pooling borders of a target elution volume as a function of the computed elution salt concentration and the application of an elution buffer having the computed salt concentration is performed for each of the steps.

For example, each of the plurality of chromatography simulations can be a simulation of a chromatography process using two or more elution steps, whereby in each elution step, an elution buffer with a different elution salt concentration is used. The computed elution buffer salt concentration is a series of different, elusion-step specific elution buffer salt concentrations. The applying of the elution buffer having the computed salt concentration on the chromatography column comprises step-wise applying a series of elution buffers having the different salt concentrations in accordance with the computed series of elusion-step specific salt concentrations.

According to embodiments, the applied protein solution comprises each of the two or more target proteins and each of the one or more further proteins, if any, in a respective concentration of at least 0.5% by weight, in particular of at least 1% by weight, in particular at least 2% by weight.

Applicant has observed that protein concentrations, in particular if within the above-specified ranges, has an impact on the elution behavior of a protein. By taking into account the concentration of each of the proteins contained in the protein solution that is applied on the column which exceed the above-mentioned threshold also referred to as "minimum amount threshold", the accuracy of the prediction of a suitable elution buffer salt concentration can be increased. The proteins applied on the column may interact with each other as well as with the stationary phase in a multitude of ways. Some proteins may block others from binding to the column resin, may compete with other proteins in respect to binding to the stationary phase, or promote their binding. By taking into account the chemical properties as well as the concentrations of all proteins contained in the protein solution (i.e., all target proteins and all further proteins whose concentration exceeds the above-mentioned minimum amount threshold, if any), the accuracy of the computations and predictions of the chromatography simulation software may significantly be increased.

Preferably, the protein solution applied on the column is a pre-purified protein solution comprising only one or more target proteins and typically also one or more nontarget proteins. For example, at first, the totality of proteins could be extracted from a cell culture, e.g. a cell culture that was modified as to produce one or more target proteins of interest. In a next step, this cell culture protein extract is pre-purified in order to obtain only a small number of proteins, preferably only the one or more target proteins and as few other proteins as possible. However, often it is not possible to obtain the one or more target proteins in a pure form in the pre-purification step. For example, the cell culture protein extract may comprise many thousand different types of proteins. In the pre-purification step, the protein extract is applied on an affinity chromatography column to obtain a limited set of proteins, e.g. all proteins having a particular protein sequence or having a particular epitope. Hence, the protein solution applied on the cation chromatography column can be a protein solution obtained by performing a pre-purification process such as affinity chromatography on a cell culture extract or other source.

For example, the proteins in the protein solution obtained as a result of the pre-purification approach with the affinity chromatography column can consist of all glycoforms of a particular protein, e.g. a glycoform being free of any glycosyl groups, a second glycoform comprising one glycosyl group, a second glycoform comprising a different type of glycosyl group, a third glycoform comprising the same glycosyl group as the first glycoform but on a different position, and so on. Optionally, the protein solution may in addition comprise further proteins which are undesired/not of interest but whose removal failed during the pre-purification step for whatever reason.

Typically, the number of protein types contained in the protein solution applied on the cation chromatography column is limited and much smaller than the protein number in a cell culture extract. For example, the number of protein types contained in the protein solution applied on the cation chromatography column is typically below 10, often below 5.

According to embodiments, the protein solution applied on the column comprises a first P1 and second P2 target protein and a further protein P3 considered as contaminating protein. The affinity of the second target protein P2 and of the further protein P3 to the stationary phase of the column is similar to the affinity of the first target protein to the stationary phase leading to overlapping elution behaviors of P1, P2 and P3.

For example, the proteins P1, P2 and P3 are glycoforms or other PTM variants of the same protein and hence have similar affinity to the stationary phase. Separating P1 and P2 from P3 and providing P1 and P2 in a desired ratio was typically not feasible for state of the art cation chromatography approaches. Embodiments of the invention may allow predicting a suitable elution salt concentration first and then predicting, based on this optimum salt concentration and other parameter values the pooling borders in a particularly accurate way that allows to separate target proteins more exactly from other proteins or—in case this is physically not possible are the peaks are strongly overlapping—allows at least to collect a target elution volume that comprises the two target proteins P1 and P2 in a desired ratio with an acceptable degree of purity (in respect to a contamination with P3).

According to embodiments, the total amount of protein in the protein solution applied to the column is identical to or smaller than the maximum protein load capacity of the column, and is in particular in the range of 50% to 100%, e.g. 50% to 90%, of the maximum protein load capacity.

Applicant has observed that within this amount range, the chromatography procedure is particularly sensitive to the concentrations and chemical properties of the proteins contained in the applied protein solution. By taking into account the amount of each of the proteins contained in the applied protein solution, the prediction accuracy in respect to the most suitable elution salt concentration was observed to be increased significantly.

According to embodiments, the computed pooling borders of the target elution volume are specified in the form of a collection start time offset and a collection stop time offset. The method comprises:

continuously monitoring, by an automated chromatography system comprising the chromatography column, the time lapsed since the starting of the elution;

automatically starting the collecting of the eluted elution buffer by the chromatography system when the lapsed time equals the collection start time offset; and stopping the collecting of the eluted elution buffer by the chromatography system when the lapsed time equals the collection stop time offset.

According to embodiments, the method comprises inputting the amount of each of the first and second target proteins comprised in the applied protein solution and optionally also the amount of each of one or more further proteins comprised in the applied protein solution, if any, into the chromatography simulation software.

The simulations are computed as a function of a set of parameter values comprising at least:

the dimension of the provided cation exchange chromatography column; for example, the length, diameter and height or the total volume could be provided; it is also possible to select one of a set of predefined column types whose dimension are known to the chromatography simulation software; and the amounts of the first and second target proteins and optionally also the amounts of the one or more further proteins applied on the column. For example, the amounts of the first and second target proteins and of any further protein comprised in the protein solution can be measured before the computing of the simulations by suited protein analytics e.g. total protein amount by UV measurement at 280 nm; the slightly different molecular weights of the different proteins applied on the column which result from different glycosylation pattern can be determined by cation exchange high performance liquid chromatography (CEX-HPLC). This molecular weight information can be used e.g. in order to compute the number of protein molecules/the molar concentration of a particular protein applied on the column and/or to verify whether the target protein ratio in the target elution volume meets e.g. the requested amount, ratio or purity.

Applicant has observed that the amount of protein applied on the column may vary significantly from case to case. Taking into account the amount of the individual proteins that are applied on the column as well as the column dimension may allow computing and predicting an elution buffer salt concentration that is best suited for obtaining a target elution volume comprising the target proteins in a desired amount and/or purity particularly accurately. Then, this particular computationally determined salt concentration is used as the salt concentration of the elution buffer actually used for performing the chromatography procedure. In addition, the computationally determined elution buffer salt concentration is used for predicting the pooling borders of a target elution volume that comprises the target proteins in the desired amount and/or purity. The computationally predicted pooling borders can be output to a human or to an automated elution buffer collection unit, thereby facilitating the obtaining of the one or more target proteins in the desired amount and/or purity.

Hence, the elution buffer obtained by embodiments of the invention is not a "standard"/"one fits all" elution buffer, but is rather an elution buffer specifically adapted to the type and amount of proteins contained in the protein solution and adapted to the dimensions of the column. Applicant has observed that adapting the elution salt concentration to the column used and to the amounts of the proteins applied on the column in each individual case may greatly increase the ability of a chromatography column separate different proteins.

According to embodiments, the simulations are performed as a function of both multiple different salt concentrations (which may also be referred to as "candidate salt concentrations") and multiple different elution buffer pH values (which may also be referred to as "candidate pH values"). As a result of the simulations, a combination of a particular salt concentration and pH value is identified that meets the optimization criterion best. This pair of salt concentration and pH value is used as the salt concentration and pH value of the elution buffer that is actually used to elute the proteins.

According to embodiments, the set of parameters further comprises:

a predefined pH value of the elution buffer; for example, the pH value can be the pH value of an elution buffer having already been successfully used for eluting the target proteins or a similar protein previously;

a flow rate of the elution buffer through the column;

chemical properties of the proteins of the applied protein solution.

The flow rate of the elution buffer through the column can be the flow rate set by an elution buffer pump that is configured to pump the elution buffer through the column at a preset rate. The flow rate can be specified e.g. in ml/minute. The flow rate can also be specified e.g. in mm/sec as the column diameter is known and allows deriving a flow rate in ml/min from the mm/sec value.

In some embodiments, the flow rate generated by the pump can be set by a user by configuring the pump. In some embodiments, the user enters the elution buffer flow rate (that may be displayed on a display of the pump) manually in the chromatography simulation software for each chromatography run. In other embodiments, the elution buffer flow rate is stored in a configuration file of the chromatography simulation software and is re-used for multiple chromatography runs until the user modifies the elution buffer flow rate in the configuration file of the chromatography simulation software and in the settings of the pump.

Taking into account not only the amounts but also the chemical properties of the target proteins and optionally also the one or more further proteins applied to the column may further increase the accuracy of the simulations and the predictions.

According to embodiments, the pooling borders actually output to the user may be converted into a different format to ease understanding. For example, the collection start time offset and the collection stop time offset could be specified as time offsets starting from the begin of the "280 nm peak" (indicating the peak of total protein concentration in the eluate) that can be predicted also and can be empirically compared with an optically measured 280 nm peak signal. Likewise, the collection start time offset and the collection stop time offset can be specified in "column volumes".

Many different computational approaches for simulating a cation-chromatography run and for predicting the elution profile of a particular protein exist and can be used for performing the simulations and for predicting the target elution borders according to embodiments of the invention.

For example, Wittkopp F, Peeck L, Hafner M, Frech C. in "Modeling and simulation of protein elution in linear pH and salt gradients on weak, strong and mixed cation exchange resins applying an extended Donnan ion exchange model" in J Chromatogr A. 2018; 1545:32-47. doi:10.1016 describe the application of a Donnan equilibrium ion exchange (DIX) model for modeling and simulation of ion exchange chromatography of a monoclonal antibody in linear chromatography. The publication deals with the description of the conditions inside a chromatography column at low protein concentrations but does not relate to the optimization of a protein separation.

According to another example, Müller-Späth T, Ströhlein G, Aumann L, et al. in "Model simulation and experimental verification of a cation-exchange IgG capture step in batch and continuous chromatography", J Chromatogr A. 2011; 1218(31):5195-5204, doi:10.1016 describe the simulation of a cation-exchange capture step of a monoclonal antibody (mAb) purification process using single column batch and multicolumn continuous chromatography (MCSGP) based on a lumped kinetic model using model parameters such as porosities, retention factors and mass transfer parameters of purified mAbs.

According to embodiments, the chromatography simulation software is configured to use a combination of mathematical models for computing the simulations and/or for computing the pooling borders of the target elution volume. The models comprises:

- a column model being configured to interrelate the concentration of each of the proteins, the salt concentration and the pH-value in the elution buffer in the interstitial volume of the column; and
- a pore model being configured to interrelate the concentration of each of the proteins, the salt concentration and the pH value in the elution buffer in the pore volume of the stationary phase of the column; and
- a reaction model being configured to interrelate the concentration of each of the proteins in the stationary phase, the elution buffer salt concentration and at least some of the chemical properties of each of the (target and optionally further) proteins in the protein solution.

A plurality of different column models, pore models and reaction models are described in the literature. Many of these models are continuously refined. A list of references describing examples of models that can be used in the context of this invention is disclosed e.g. in the description of FIG. 4C.

For example, the column model can be implemented in accordance with Schmidt Traub et al., "Preparative Chromatography" 2012, Viley-VCH. The pore model can be implemented in accordance with Schmidt Traub et al., "Preparative Chromatography" 2012, Viley-VCH. The reaction model can be implemented in accordance with Kluters et al., "Application of linear pH gradients for the modeling of ion exchange chromatography: separation of monoclonal antibody monomer", J Sep Sci, 2016 February, 93(4), 663-675. The parameters of the reaction model and/or the model itself can be modified at various levels of complexity to facilitate the description of experimental data. This is for instance demonstrated in "Modeling of complex antibody elution behavior under high protein load densities in ion exchange chromatography using an asymmetric activity coefficient" Biotechnol. J., 12: 1600336. doi:10.1002/biot.201600336 by Huuk et el. This publication describes how a generalized ion-exchange isotherm can be used for the modeling a separation of a single protein species at high protein loading conditions.

The pore model, the column model and the reaction model are interconnected via the salt concentration and protein concentration. The column model and pore model are interconnected by the salt concentration $$\frac{\partial c_{SALT}}{\partial t}(x, t),$$

hence the equation of the pore model can be inserted into the column model.

The first equation of the reaction model can be inserted via the $$\frac{\partial q_{PROT\_i}}{\partial t}$$

term into the column model. The parameters describing the binding strength and hence chemical properties of the protein are the equilibrium constant $K_{eq}$ and the number of binding sites v. Both are dependent from the pH via the v (second equation of the reaction model).

Hence, the salt concentration of the elution buffer that is needed to elute the desired amount, ratio and/or purity of the target proteins can be calculated on the basis of a set of parameters like pH value, the amount and chemical properties of the applied proteins, the column dimension and the elution buffer flow rate defined by the pump.

The protein amount of a target protein or of an optional further protein is the integral over time of the concentration of this protein in the mobile phase leaving the chromatography column. The calculation software varies the salt concentration $c_{SALT}$ and performs predictions of the elution profiles of the target proteins and optionally also of one or more further as a function of the salt concentration for identifying the salt concentration which provides for protein elution profiles which match the optimization criterion best.

Column Model

According to embodiments, the interrelation specified in the column model comprises a column model formula according to:

$$\frac{\partial c_{SALT}}{\partial t}(x,t) + \frac{u_{int}(t)}{\varepsilon_{col}}\frac{\partial c_{SALT}}{\partial x} +$$

$$\frac{1-\varepsilon_{col}}{\varepsilon_{col}}\left(\varepsilon_p\frac{\partial c_{PROT_i}}{\partial t} + (1-\varepsilon_p)\frac{\partial q_{PROT_i}}{\partial t}(x,t)\right) = D_{ax}\frac{\partial^2 c_{SALT}}{\partial x^2}(x,t). \quad 10$$

Thereby, i is an index for a particular protein, t is time, x is the position in the column along the vertical column axis, $c_{SALT}$ is the concentration of the free (unbound) salt ion (typically Na+ for cation exchange chromatography) in the mobile phase (i.e., the elution buffer phase comprising neglectable amounts of the applied protein solution) of the column, $c_{PROT\_i}$ is the concentration of the protein i in the mobile phase of the column, $q_{PROT\_i}$ is the concentration of the protein i bound in the stationary phase, $u_{int}$ is the interstitial flow velocity defined as the velocity obtained by flow through the column between the stationary phase particles, $\varepsilon_{col}$ is the interstitial porosity (the open pore area in the column's cross section). It is defined as the ratio of interstitial volume and column volume, whereby the interstitial volume is the elution buffer volume in the column outside of the particles), $\varepsilon_p$ is the particle porosity (defined as the particles own internal porosity (pore volume)), $D_{ax}$ is the axial dispersion coefficient. The axial dispersion coefficient is a measure of the degree of spread of an inert trace material along the column's longitudinal direction. $D_{ax}$ describes the dispersion in axial direction as described in Fick's law.

The porosities $\varepsilon_{col}$, $\varepsilon_p$ and the dispersion coefficient $D_{ax}$ are parameters which can influence the separation of the elution protein peaks. The porosities usually are fixed and are determined by the chromatography resin comprised in the column. Preferably, they are stored as default values, e.g. in a configuration file, but can be modified in case a different stationary phase material is used.

Hence, according to embodiments of the invention, the dimension of the cation exchange chromatography column is considered via the interstitial flow velocity (normalization of flow to column diameter in the pore model) as well as the position in the column reflected by the vertical column position x. The combination of length and diameter of a column defines the column's total volume.

The interstitial flow velocity is computationally derived from the flow rate of the elution buffer through the column.

For example, a user can enter the elution buffer flow rate "ebfr" in [mm/s] into the chromatography simulation software. The chromatography simulation software computes the interstitial flow velocity u(int) [mm/s] according to the following formula:

$$u(int) = ebfr/\varepsilon_{col}$$

wherein $\varepsilon_{col}$ is the interstitial column porosity (lacking a unit).

A concrete example for how to obtain the interstitial flow velocity from the elution buffer flow rate (which may be defined by the pump configured to pump the elution buffer through the column) is described in Schmidt-Traub, Henner, ed. "Preparative chromatography: of fine chemicals and pharmaceutical agents", John Wiley & Sons, 2006.

Pore Model

According to embodiments, the interrelation specified in the pore model comprises a pore model formula according to:

$$\frac{\partial c_{SALT}}{\partial t}(x,t) =$$

$$\frac{k_{eff,i}}{\varepsilon_p}\frac{z}{r_p}(c_{SALT}(x,t) - c_{PROT\_i}(x,t)) - \frac{(1-\varepsilon_p)}{\varepsilon_p}\frac{\partial q_{PROT\_i}}{\partial t}(x,t).$$

Thereby, i is an index for a particular protein, t is time, x is the position in the column along the vertical column axis, $c_{SALT}$ is the concentration of the free (unbound) salt ion in the mobile phase of the column, $c_{PROT\_i}$ is the concentration of the protein i in the mobile phase of the column, $q_{PROT\_i}$ is the concentration of the protein i bound in the stationary phase, $\varepsilon_{col}$ is the interstitial column porosity. $\varepsilon_p$ is the particle porosity, $k_{eff}$ is the effective mass transfer coefficient (describes the movement of the protein from the interstitial mobile phase into the pore volume), z a numerical value in the range of 2.7 to 3.3, in particular 3.0, $r_p$ is the radius of the chromatography beads. The parameter z depends on geometry aspects of the column material. A concrete example for how to obtain parameter z is described in Schmidt-Traub, Henner, ed. Preparative chromatography: of fine chemicals and pharmaceutical agents. John Wiley & Sons, 2006, page 338-339.

According to one example, the interstitial flow velocity can be related to the flow rate of the elution buffer through the column as follows:

The flow rate through the column, also referred to as volumetric flow $u_p$ (ml/min), describes the volume of mobile phase which is pumped through the column. For the normalization of the flow rate to the chromatography column dimension, the flow rate can be normalized in respect of the column diameter using the column volume and length. The unit of the flow velocity u changes to (mm/s) according to the following formula:

$$u\left[\frac{mm}{s}\right] = \frac{L_{col}}{V_{col}} * \frac{u_p\left[\frac{ml}{min}\right]}{60}$$

The interstitial flow velocity additionally normalizes the flow velocity regarding the porosity of the chromatography beads by only considering the interstitial column volume $V_{interstitial}$ (i.e., only the volume between the porous chromatography beads). The ratio of the interstitial volume and the total column volume of the chromatography column used is $\varepsilon_{col}$:

$$\varepsilon_{col} = \frac{V_{interstitial}}{V_{total\_column}}$$

The parameter $\varepsilon_{col}$ thereby is the fraction of the interstitial volume and the total column volume.

The stationary phase of a column can be described as a matrix of beads. The total volume of all the beads in the column is referred to as "bead volume" $V_{beads}$ whereby the volume of each bead comprises both the volume consumed by the stationary phase material of the bead and the volume of the pores comprised in the bead. The interstitial volume $V_{interstitial}$ of a chromatography column is defined as the total volume of the column $V_{col}$ minus the total bead volume of all beads comprised in the column $V_{beads}$. According to embodiments, the column model and the core model are combined. For example, according to embodiments, the computing of the target elution volume as a function of at least the computed salt concentration comprises using the column model formula and the pore model formula for computing the concentration of protein i in the interstitial volume can as a function of the salt concentration $c_{SALT}$ and of the concentration $q_{PROT\_i}$ of the protein i in the stationary phase.

According to embodiments, the computing of the pooling borders of the target elution volume as a function of at least the computed salt concentration comprises using the column model formula and the pore model formula for computing the concentration of the first target protein at the position x=column length at multiple different elution times t.

Reaction Model

According to embodiments, the interrelation specified in the reaction model comprises:

a first reaction model formula according to:

$$k_{kin}\frac{\partial q_{PROT\_i}}{\partial t} = K_{eq,i}\left(\Lambda - \sum_{i=1}^{n}(v_i + \sigma_i)q_{PROT\_i}\right)^{v_i}c_{PROT\_i} - q_{PROT\_i}c_{SALT}^{v}$$

a second reaction model formula according to:

$$v_i(\text{pH}) = \frac{-N_{carb,i}}{1 + 10^{pK_{a_{carb}} - pH}} + \frac{N_{his,i}}{1 + 10^{pH - pK_{a_{his}}}} + \frac{N_{N-term,i}}{1 + 10^{pH - pK_{a_{N-term}}}} + \frac{N_{ami,i}}{1 + 10^{pH - pK_{a_{ami}}}}$$

a third reaction model formula according to:

$$\ln(K_{eq,i}) = \frac{-\Delta G_P^0}{RT} + v_i(\text{pH})\frac{\Delta G_S^0}{RT}.$$

Thereby, i is an index for a particular protein, t is time, x is the position in the column along the vertical column axis, $c_{SALT}$ is the concentration of the free (unbound) salt ion in the mobile phase of the column, $c_{PROT\_i}$ is the concentration of the protein i in the mobile phase of the column, $q_{PROT\_i}$ is the concentration of the protein i bound in the stationary phase, $K_{kin}$ is the kinetic rate (defined as the reciprocal value of the desorption rate and describing the speed of reaction of proteins displacing ions from the stationary phase's ligands), Keq is the equilibrium constant (i.e., the molar concentration of a particular protein i in the stationary phase divided by the molar concentration of the protein i in the mobile phase), $\Lambda$ is the ligand density (defined as the number of ligands in mol per column volume), $v_{\_i}$ is the number of binding sites (i.e., the number of binding sites of protein i participating in protein binding to the stationary phase), $\sigma_{\_i}$ is the shielding factor (i.e., the number of ligands per bound protein molecule of protein i which is shielded when the protein i binds to the stationary phase), N_(carb,i) is the number of carboxy sites of the protein i which interact with the stationary phase, N_(his,i) is the number of histidine sites of the protein i which interact with the stationary phase, N_(N-term,i) is the number of N termini sites of the protein i which interact with the stationary phase, N_(ami,i) is the number of amino sites of the protein i which interact with the stationary phase, pH is the pH value of the elution buffer, $$-\Delta G_P^0$$

is the difference in standard free Gibbs enthalpy between absorbed and unbound state of the protein i, $$\Delta G_S^0$$

is the difference in standard free Gibbs enthalpy between absorbed and unbound state of the salt, $pK_{a_{carb}}$ is the average acid dissociation constant (Ka) of all carboxyl-groups of the protein i which interact with the stationary phase, $pK_{a_{his}}$ is the average Ka of all histidine-amino-acids of the protein i which interact with the stationary phase, $pK_{a_{N-term}}$ is the average Ka of all N-terminal $\alpha$-amino groups of protein i which interact with the stationary phase, $pK_{a_{ami}}$ is the average Ka of all amino groups of protein i, R is the gas constant, and T is the temperature of the column and the elution buffer. The concentration of a particular protein "i" in the stationary phase ("$q_{PROT}(i)$") is computed as a function of the pH value of the elution buffer by resolving the third reaction model formula to $q_{PROT}(i)$ using the first and the second reaction model formula.

The salt concentration $c_{SALT}$ influences the amount of protein $q_{PROT\_i}$ bound in the stationary phase via the first reaction model formula: At low salt concentrations the protein binds to the chromatography column, at higher salt concentrations the protein is displaced by salt ions and eluted. Depending on the binding strength of the protein, which in the reaction model is composed of the number of binding sites v and the equilibrium constant $K_{eq}$, proteins elute at different salt concentrations. By selecting an appropriate salt concentration, the target protein can be eluted while unwanted proteins remain bound on the chromatography column. Some of these parameter values are protein specific and can be derived from literature. Some of these parameters are protein and model specific. They may also be derived from literature or can be obtained by performing some preliminary empirical calibration steps which are typically described by the authors having published the respective model used. For example, parameters like N_(carb,i) indicating the number of carboxy sites of the protein i which interact with the stationary phase is protein specific but also depend on the model used for performing the simulation. The number of carboxyl sites actually interacting with the stationary phase is limited by sterical effects which are described in the reaction model used. The number of the respective sites interacting with the stationary phase are determined using protein specific and model specific empirical tests. For some proteins, the parameter values can already be derived from literature. The Gibbs energy $\Delta G_P^0/RT$ and $\Delta G_S^0/RT$ may also be determined empirically for each of the proteins in the protein solution or may be derived from literature.

The pH value influences the number of binding sites v of the protein (second equation). The number of binding sites v influences the equilibrium constant Keq (third equation). Thereby, the pH value is linked to the salt concentration of equation 1 of the reaction model.

Hence, the reaction model takes into account the pH value and the contribution of the chemical properties of the proteins, e.g. in terms of the pKa's of certain groups in the protein and in terms of the protein's binding sites v. The reaction model also takes into account the salt concentration, thereby interrelating an elution buffer salt concentration with chemical properties of the proteins to be eluted. The salt concentration $c_{SALT}$ is part of the first equation where it is directly connected to the proteins binding characteristics via the number of binding sites v.

However, the reaction model described above is only one out of many possible ways how a reaction model can be implemented. The modeling and simulation of cation chromatography runs is an ongoing field of research, so various modifications of the formulas and models described herein for performing the simulations may likewise be used. It is also possible to use alternative column, pore and reaction models currently described in literature, and it is possible that in the future new column, pore and reaction models will be developed and published which can likely be used for performing chromatography simulations as a function of at least several different elution buffer salt concentrations and preferably as a function of further parameters such as the amount and the chemical properties of the proteins to be applied on the column.

According to one embodiment, the following model-specific chemical property values of the proteins P1-P3 described e.g. with reference to FIG. 7 are provided and used as input by the reaction model during the computation of the suited elution buffer salt concentration and the pooling borders:

|  | Variant P1 | Variant P2 | Variant P3 |
|---|---|---|---|
| Film Diffusion $k_{eff}$ [mm/s] | 0.0026 | 0.0452 | 0.0159 |
| Kinetic [s(M)$^v$] | 0.0069 | 0.0023 | 0.0051 |
| $\Delta G_p^0/RT$ | 2.05 | 2.28 | −0.05 |
| $\Delta G_s^0/RT$ | 0.08 | 0.08 | 0.08 |
| N_(carb,i) | 6.09 | 5.10 | 6.95 |
| N_(his,i) | 0.83 | 2.71 | 1.52 |
| N_(ami,i) | 9.94 | 11.71 | 12.80 |
| N_(N-term,i) | 1.43 | 2.43 | 2.49 |
| Shielding σ_i | 120.58 | 98.07 | 92.45 |

In addition, the following input parameter value can be provided to the reaction model e.g. via a GUI, a configuration file or other data source:

| Variable | Value | Unit |
|---|---|---|
| Axial Dispersion Coefficient Dax | 0.2 | mm2/s |
| Bead porosity $\varepsilon_P$ | 0.69 | — |
| Interstitial column porosity $\varepsilon_{col}$ | 0.43 | — |
| Ligand density | 0.673 | mol/L solid adsorber |

The shielding factors becomes smaller from variant 1 to variant 3 which is consistent with the grade of decreasing glycosylation and thus protein size from variant 1 to variant 3.

The above-mentioned parameter values can be provided by a user via a GUI and/or can be specified in a configuration file of the chromatography simulation software.

Various approaches exist for obtaining and/or estimating model parameters. For example, the research article "Application of linear pH gradients for the modeling of ion exchange chromatography: Separation of monoclonal anti-body monomer from aggregates" of Simon Kluters et al., first published on 9 Nov. 2015 (https://doi.org/10.1002/jssc.201500994) describes a mechanistic model of ion exchange in a chromatography column and how the parameters of this model can be obtained.

In a further aspect, the invention relates to a chromatography control system comprising a simulation software. For example, the chromatography control system can be used for guiding manual control of a chromatography system, or for providing fully automated or semi-automated control of the control system. The simulation software is configured for performing a method of obtaining pooling borders of a target elution volume comprising a desired first amount of a first target protein. The chromatography control system is configured for:

receiving an optimization criterion and inputting the optimization criterion into the chromatography simulation software, the optimization criterion being a desired property of the target elution volume in respect to the first and second target proteins comprised in the target elution volume;

computing, using the chromatography simulation software, an elution buffer salt concentration adapted to elute the first and the second target protein from the chromatography column such that a target elution volume can be obtained that matches the optimization criterion best, the computing comprising computing a plurality of chromatography simulations as a function of multiple different elution buffer salt concentrations;

computing the pooling borders of the target elution volume as a function of at least the computed salt concentration and the input optimization criterion;

outputting the computed salt concentration and pooling borders and/or controlling an elution volume collection unit such that the computed target elution volume is automatically collected as a separate fraction in accordance with the computed pooling borders.

According to embodiments, the system is further configured for:

receiving dimensions of a cation exchange chromatography column; and receiving the amounts of the first and second target proteins and optionally also the amounts of the one or more further proteins applied on the column;

The simulations and/or the pooling borders are computed as a function of a set of parameter values comprising at least:

the dimension of the provided cation exchange chromatography column; and the amounts of the first and second target proteins and optionally also the amounts of the one or more further proteins applied on the column.

According to embodiments, the set of parameters further comprises:

a predefined pH value of the elution buffer, a flow rate of the elution buffer through the column;

chemical properties of the proteins of the applied protein solution.

According to embodiments of the invention, the desired first amount of the first protein is specified as a desired absolute amount of the desired first protein. In particular, the desired amount of the first target protein can be specified in the form of a desired concentration of the first protein in a collected volume of the elution buffer or a derivative value thereof.

According to other embodiments, the applied protein solution comprises the first target protein, a second target protein and zero, one or more of the further proteins. The desired first amount of the first protein is input into the chromatography simulation software in the form of a relative amount. The relative amount is a ratio of the first target protein and the second target protein. The chromatography simulation software computes the pooling borders of the target elution volume as a function of at least the computed salt concentration and the input desired ratio. The method is used for producing a target elution volume comprising the desired ratio of the first and second target proteins.

According to embodiments, the plurality of chromatography simulations are computed as a function of the multiple different elution buffer salt concentrations and as a function of multiple different elution buffer pH values. The computing of the salt concentration comprises computing a combination of an elution buffer salt concentration and an elution buffer pH value which in combination are adapted to elute the first and the second target proteins from the chromatography column such that a target elution volume can be obtained that matches the optimization criterion best. The chromatography simulations are performed for identifying the combination of the combination of the elution buffer salt concentration and the elution buffer pH value. The computing of the pooling borders of the target elution volume is computed as a function of at least the computed combination of the elution buffer salt concentration and the elution buffer pH value and the input optimization criterion. The computed pH value is output in addition to the computed elution buffer.

According to embodiments, the chromatography control system is configured to control a buffer mixing unit as to automatically generate an elution buffer having the output elution salt concentration.

In addition, or alternatively, the chromatography control system is configured to control an elution buffer selection unit adapted to automatically select one out of a plurality of available elution buffers having different salt concentrations, the selected elution buffer having the output salt concentration.

In addition, or alternatively, the chromatography control system is configured to control a buffer mixing unit as to automatically generate an elution buffer having both the salt concentration and the pH value computed and output in combination.

In addition, or alternatively, the chromatography control system is configured to control an elution volume collection unit of a chromatography system such that the computed target elution volume is automatically collected as a separate fraction in accordance with the computed pooling borders.

In addition, or alternatively, the chromatography control system is configured to control an elution buffer selection unit adapted to automatically select one out of a plurality of available elution buffers having different salt concentrations and different pH values, the selected elution buffer having both the salt concentration and pH value computed and output in combination.

In addition, or alternatively, the chromatography control system is configured to control a buffer application unit configured to automatically apply an automatically generated or selected elution buffer on the chromatography column, the applied elution buffer having the output salt concentration or having both the salt concentration and pH value computed and output in combination.

In a further aspect, the invention relates to a chromatography system comprising the chromatography control system and further comprising a buffer mixing unit and/or the elution buffer selection unit and/or the buffer application unit and/or the automated elution volume collection unit mentioned above.

In a further aspect, the invention relates to a chromatography system comprising the chromatography control system and further comprising a buffer mixing unit adapted to automatically generate an elution buffer having the output elution salt concentration.

In addition or alternatively, the chromatography system further comprises an elution buffer selection unit adapted to automatically select one out of a plurality of available elution buffers having different salt concentrations, the selected elution buffer having the output salt concentration.

In addition or alternatively, the chromatography system further comprises a buffer application unit configured to automatically apply the automatically generated or selected elution buffer on the chromatography column.

In addition or alternatively, the chromatography system further comprises an automated elution volume collection unit configured to automatically start and stop collecting a fraction of the eluted buffer leaving the column in accordance with the output pooling borders.

In a further aspect, the invention relates to a computer program for managing a chromatography process such that a target elution volume comprising a first and a second target protein is obtained. The computer program comprises a chromatography simulation software and is configured for:

receiving an optimization criterion being a desired property of a target elution volume in respect to a first and second target proteins comprised in the target elution volume;

computing, using the chromatography simulation software, an elution buffer salt concentration adapted to elute the first and the second target proteins from the chromatography column such that a target elution volume can be obtained that matches the optimization criterion best, the computing comprising computing a plurality of chromatography simulations as a function of multiple different elution buffer salt concentrations;

computing the pooling borders of the target elution volume as a function of at least the computed salt concentration and the input optimization criterion; and outputting the computed salt concentration and/or the pooling borders for enabling a user to control a chromatography system such that a target elution volume comprising the first and the second target proteins in accordance with the optimization criterion is obtained and/or using the computed salt concentration and/or the pooling borders for automatically or semi-automatically controlling a chromatography system such that a target elution volume comprising the first and the second target proteins in accordance with the optimization criterion is obtained.

According to embodiments, the computer program is further configured for generating control commands for automatically or semi-automatically controlling one or more units of a chromatography system.

According to embodiments, the computer program is further configured for generating control commands for automatically or semi-automatically controlling one or more units of a chromatography system.

A "target protein" as used herein is a protein or protein variant with a particular PTM which shall be obtained by means of cation chromatography in a desired absolute or relative amount.

An "elution profile" of a protein as used herein is an indication of the concentration of the protein in an eluate over a period of time.

The one or more "further proteins" contained in the applied protein solution can comprise one or more further target proteins and/or one or more non-target proteins, whereby a "non-target protein" is a protein whose presence is undesired, e.g. because it is considered as a contamination that is to be removed from the one or more target proteins during the chromatography run.

The "target elution volume" as used herein is a particular volume of the target buffer that has passed the chromatography column and has afterwards been collected after having left the column. The target elution volume comprises the one or more target proteins in a desired absolute or relative amount. The target elution volume is determined by An "ion exchange chromatography" as used herein is a chromatography process that separates ions and polar molecules such as proteins or peptides based on their affinity to the ion exchanger. However, ion chromatography must be done in conditions that are one unit away from the isoelectric point of a protein. Hence, the separation of molecules having highly similar isoelectric points at given conditions is a big challenge.

The term "cation exchange chromatography" refers to a type of ion exchange chromatography that is used when the molecule of interest is positively charged or has positive polarity. The molecule is positively charged or has positive polarity because the pH for chromatography is less than the pI. In this type of chromatography, the stationary phase is negatively charged and positively charged molecules are loaded to be attracted to it. Cation exchange chromatography is used when the desired molecules to separate are cations. The bound molecules then can be eluted from the column and collected using an eluant referred herein as "elution buffer". One of the primary advantages for the use of ion chromatography is only one interaction involved during the separation as opposed to other separation techniques.

A "chromatography simulation software" as used herein is any type of software, e.g. an application program, a script, a software module of a larger software suite or software platform that comprises computer-interpretable code for simulating (predicting) some aspects of a chromatography process, in particular a recommended salt concentration of the elution buffer and/or recommended elution borders of an elution volume comprising the desired amount(s) of one or more target proteins.

An "elution buffer" as used herein refers to a water-based solution, also referred to as "eluant" that is applied on a chromatography column in order to elute one or more molecules that are bound to the chromatography column from the column such that the eluted proteins are contained in the elution buffer that leaves the column and can be collected separately from other proteins which leave the column in a different fraction of the eluate.

The "computed target elution volume" is the elution volume predicted to comprise one or more target proteins in the input desired absolute or relative amounts. For example, the computed target elution volume can be specified via predicted pooling borders.

The predicted "pooling borders" are data values indicating which portion of the target elution buffer volume leaving the chromatography column need to be collected separately in order to obtain an elution volume comprising the one or more target proteins in the desired amount(s). According to some embodiments, the pooling borders are specified in the form of a start time indicating the time when the collection of the target elution buffer volume is to be started and in the form of a stop time indicating the time when the collection of the target volume is to be stopped. According to other embodiments, the pooling borders are specified in the form of a start elution buffer volume indicating the elution buffer volume having traversed and left the column when the collection of the target volume is to be started and in the form of a stop elution buffer volume indicating the elution buffer volume having traversed and theft the column when the collection of the target volume is to be stopped. For example, the pooling borders of the target elution volume could be "3.5 times the column volume" and "4.6 times the column volume" and the target elution volume can be obtained by selectively collecting the elution buffer leaving the column after 3.5 column volumes of the elution buffer have already been applied onto and have left the column and stopping the collection when more than 4.6 times the column volume have been applied onto and are about to leave the column. Whether the predicted pooling borders are specified as time or volume depends on the respective implementation.

A "glycoform" as used herein is any of several different forms of a glycoprotein (or glycopeptide or other biological glycoside) having different glycans attached, or having a different number or position of glycans.

The "purity" of a protein indicates the degree of the state of this protein not being mixed with anything else, in particular, with other proteins. For example, a particular protein P1 having a purity of 99% in an elution volume implies that the elution volume consists of an elution buffer fraction and a non-elution-buffer fraction, whereby 99% of the non-elution-buffer fraction consist of the protein P1 and 1% of the non-elution-buffer fraction consist of other substances, e.g. one or more other ones of the proteins P2, P3, . . . , contained in the applied protein solution. The purity of a protein is implicitly given if the concentrations of all proteins in an eluate collected within given pooling borders are known (e.g. predicted or empirically determined). The purity can be used as an optimization criterion in respect to one or more target proteins. For example, in the ideal case, the purity of all target proteins to be obtained in the target elution volume is 100%, but in fact, the optimization criterion may require a minimum purity criterion that depends on the individual case, e.g. 99% or less.

BRIEF DESCRIPTION OF THE DRAWINGS

In the following embodiments of the invention are explained in greater detail, by way of example only, making reference to the drawings in which:

FIG. 6D depicts a comparison of a predicted and a measured protein ratio;

FIG. 1 depicts a flowchart of a chromatography method according to an embodiment of the invention.

The method can be used for obtaining a target elution volume comprising a desired absolute or relative amount and/or purity of two or more target proteins. For example, the method could be performed for obtaining a target protein P1 and a target protein P2 in a certain concentration or amount, respectively, whereby the target protein P1 preferably has a minimum purity within the target elution volume. In addition, or alternatively, the method can be used for obtaining a target elution volume comprising a desired ratio of two or more target proteins.

Figure 1:
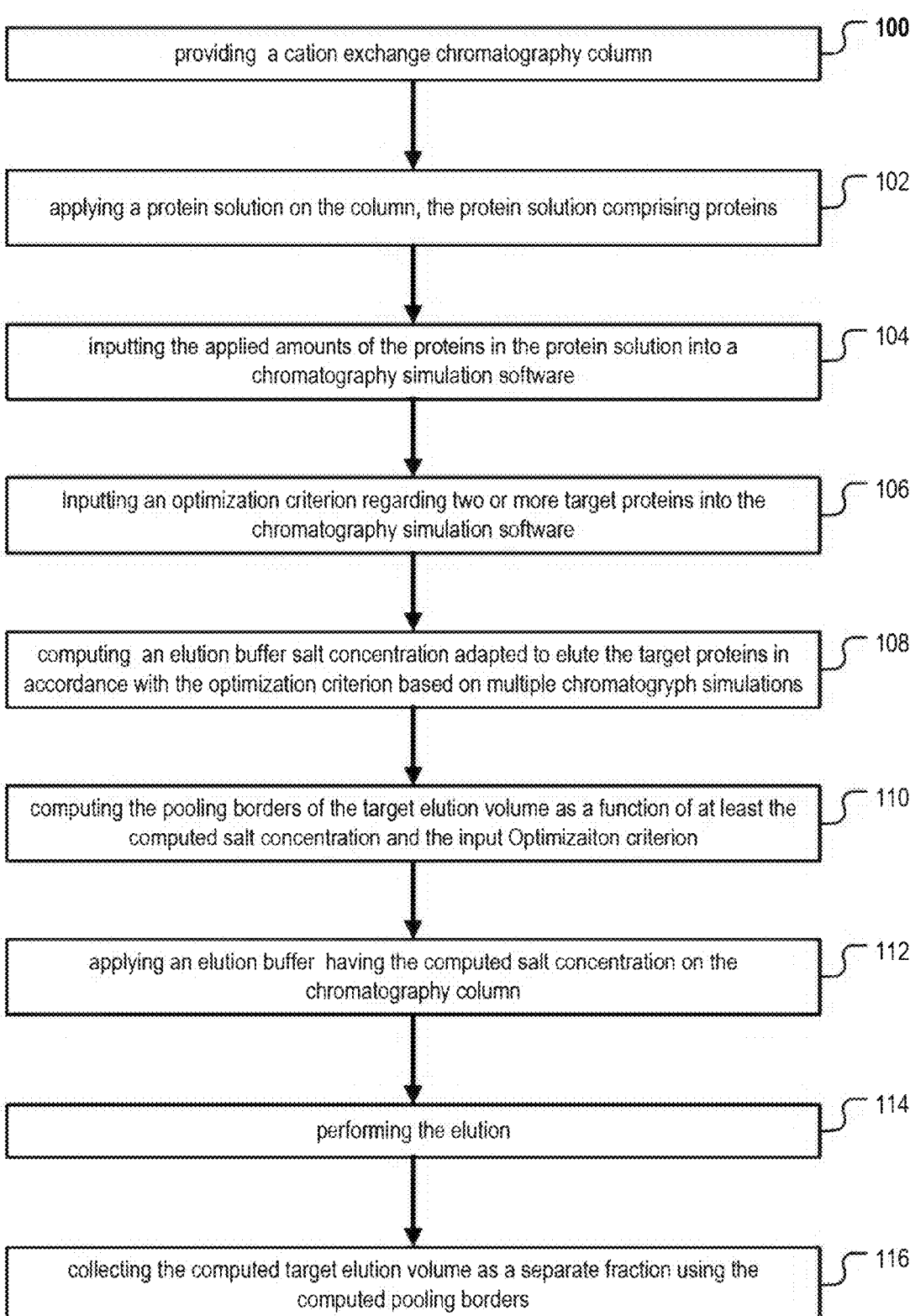
FIG. 1 depicts a flowchart of a method according to an embodiment of the invention.
Figure 2:
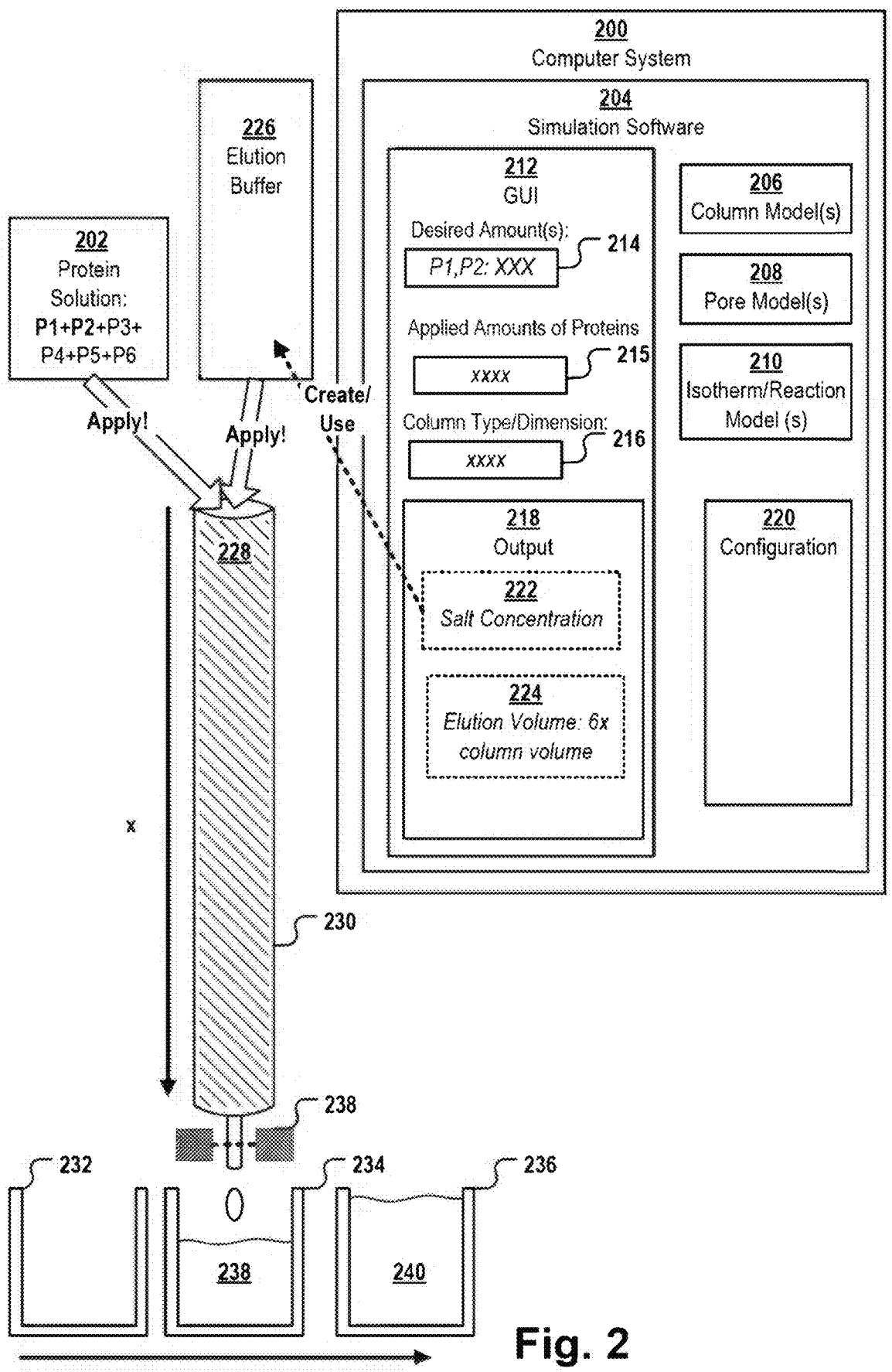
FIG. 2 depicts a chromatography system.
Figure 3:
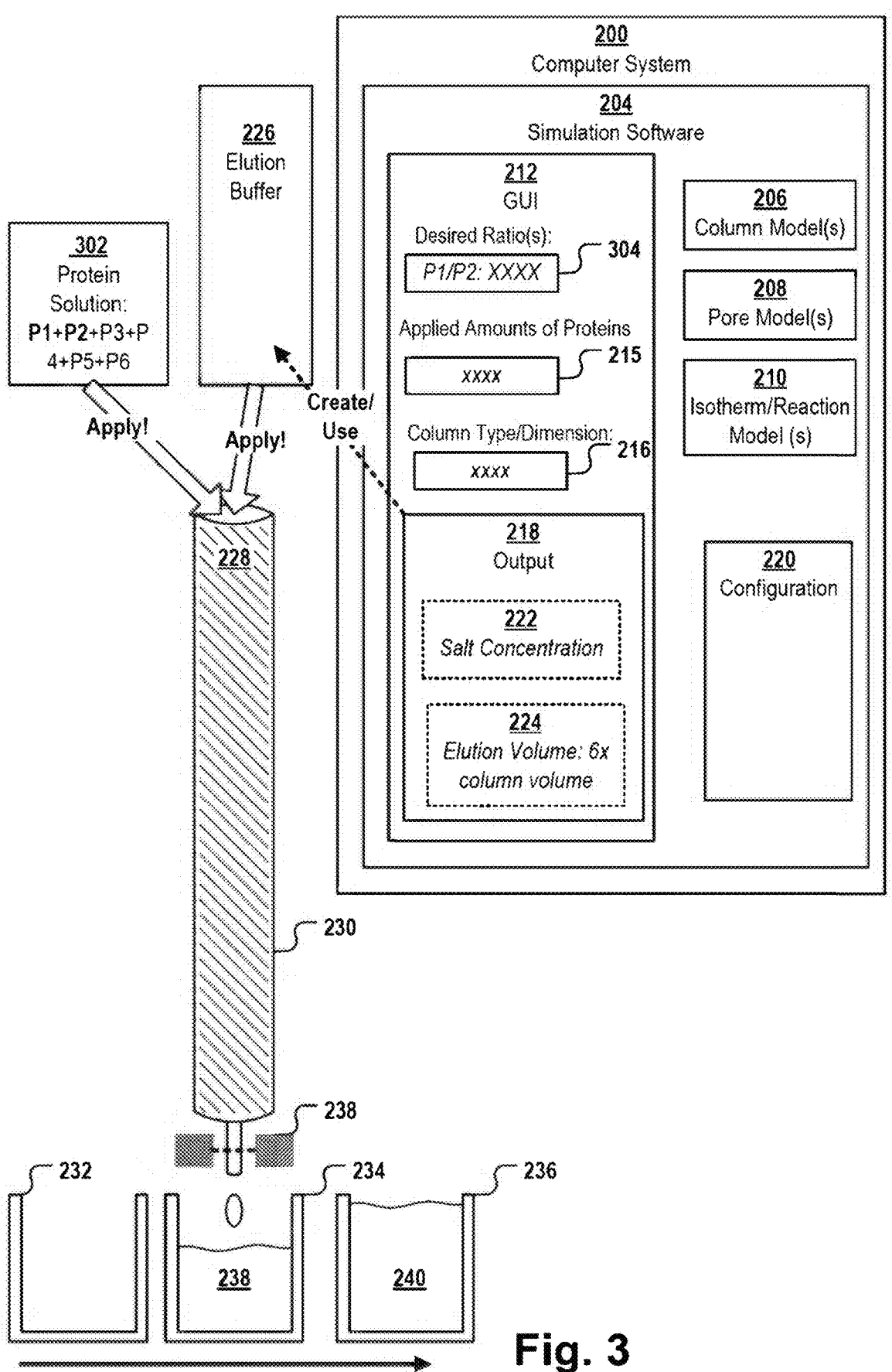
FIG. 3 depicts another chromatography system.

In a first step 100, the method comprises providing a cation exchange chromatography column 230 as depicted, for example, in FIGS. 2 and 3. There exists a large number of commercially available chromatography resin materials that can be used for fabricating self-packed columns as well as pre-packed columns.

For example, Poros™ XS (Thermo Scientific™) can be used as chromatography resin material in a self-packed column, e.g. in a chromatography column purchased from KronLab. Alternatively, a pre-packed column purchased e.g. from Repligen® (e.g. with dimensions length=5 cm and diameter=0.5 cm or length=10 cm and diameter=0.5 cm) purchased from KronLab can be used. For large scale runs, the column dimensions may be significantly different from the column dimensions for smaller, lab-scale runs. For example, the column dimension of a column used in a large scale run can be length=22.5 cm and diameter=25 cm.

The chromatography column may be installed within an automated or semi-automated chromatography system such as the ÄKTA Avant 25 and 150 chromatography systems (GE Healthcare) with a sample pump and internal fractionation.

Next in step 102, a protein solution comprising two or more target proteins and optionally one or more non-target proteins (considered as impurities) is applied on the column. The protein solution comprises the first target protein P1, the second target protein P2, and optionally one or more further proteins which are non-target proteins P3, P4, P5, P6.

To generate the protein solution to be applied on the chromatography column, one or more pre-processing and pre-purification steps are performed. At first, a cell culture is harvested and the proteome of the harvested cells is obtained. It comprises a complex mixture of glycosylated antibodies and many other types of proteins. In order to selectively obtain the antibody fraction, the cell culture extract is applied on a first pre-purification column adapted to selectively bind antibodies and antibody fragments.

According to one example, the first pre-purification column comprises a resin for monoclonal antibody (mAb) purification, e.g. Protein A resin which was equilibrated prior to the loading of the sample. The load density of the first pre-purification column in this and many other examples is about 23 g protein per liter resin. The antibody fraction was eluted and after a viral inactivation step the pH of the eluate was increased again. The solution was incubated overnight at 4° C. and filtrated over a 0.2 μm sterile filter. The filtrated Protein A eluate was used as the load material to a second pre-purification column, e.g. a column filled with a mixed mode chromatography resin. To remove protein impurities, the mixed mode chromatography was used. The column was equilibrated before loading. The load density was 25 g protein per liter resin and the flow rate 150 cm per hour. Afterwards the pH of the flow through eluate was decreased and the pool was filtrated over a 0.2 μm sterile filter.

As a result of these pre-processing and pre-purification steps, the protein solution is obtained that is to be applied on the chromatography column 230. The protein solution comprises only a few types of proteins whose chemical nature is typically well known due to the number and nature of the pre-purification steps used. The nature and number of the pre-processing and pre-purification steps may depend on the type of cell culture and cells used to provide the cell culture protein extract and/or may depend on the one or more types of proteins of interest. Typically, also a series of multiple purification steps will not be able to purify the one or more target proteins completely, in particularly not if the target protein or proteins is/are a glycoform or other type of PTM-based protein variant whose chemical properties are highly similar to one or more other proteins in the cell culture extract.

In addition, analytical tests such as mass spectroscopy may be used in order to determine not only the number but also the amount of each protein type contained in the protein solution to be applied on the column 230.

Then in step 104, the amount of each protein in the protein solution that is already applied or that is to be applied on the column, is input into a chromatography simulation software 204.

In addition, in step 106 the desired first amount 214 of the first and second target proteins and optionally also the respective amounts of the non-target proteins, if any, is input by a user into the chromatography simulation software. In addition, some other values can be input via a user interface to the chromatography simulation software or can be provided via a configuration file or other means. For example, these other values can comprise a desired optimization criterion (amount and/or purity of the first and/or second target proteins), the pH value of the elution buffer, the elution buffer flow rate specified in a pump to be used for pumping the elution buffer through the column, chemical properties of each of the proteins in the protein solution, the amounts of the individual proteins in the protein solution that has already been applied or that is to be applied on the column; and the dimension of the column. The number and nature of the parameters may depend on the models used by the simulation software for simulating the chromatography runs at multiple different elution buffer salt concentrations.

Some input parameters such as protein amount, column dimensions, the pH value of the elution buffer, the porosity of the stationary phase, the elution buffer flow rate etc. can be stored in a configuration file or entered via a GUI and can be adapted to the respective application scenario and protein solution. Some parameters like the calibrated model parameters (e.g. isotherms, N, $\Delta Gp^0$, $\Delta Gs^0$, pKa, ligand density) can be re-used and are typically stored in a configuration file.

This may enable the chromatography simulation software to simulate concentration and/or purity values of one or more target proteins for one or more different candidate elution volumes as a function of many different candidate elution buffer salt concentrations and based specifically on the amounts and chemical properties of the proteins that are to be loaded onto the column.

For example, the salt in the elution buffer whose concentration is computed can be a sodium-salt, e.g. sodium-acetate.

The recommended pH value of the elution buffer can be derived e.g. from literature or from preliminary empirical tests. For protein chromatography in general, a pH range of the elution buffer between pH 2.5 and 10 is usual. For cation exchange chromatography, a pH range of the elution buffer between pH 4 to 9 is usual. Preferably, the pH value that is input to the simulation software is a pH value known to work well for performing chromatographic separation or analysis of similar proteins like those currently to be separated. In the example described here, the pH value that is input to the chromatography simulation software and that is also the pH value of the actually used elution buffer is in the range of 5.30 to 5.70.

Typically, the pH value is not varied during the simulation. The pH value of the elution buffer that is actually used can be controlled e.g. with a pH meter, e.g. with a WTW Sentix Mic probe.

The chemical properties of the proteins can comprise properties which are independent of any predictive model used for simulating the chromatography process for computing a suitable elution buffer salt concentration (e.g. pKs or the number and nature of amino acid moieties).

The chemical properties of the proteins can in addition comprise properties which are specific for the predictive model used for simulating the chromatography process.

In order to obtain model-specific chemical properties of the proteins, chromatography data (chromatograms) as well as corresponding offline analytical data (e.g. HPLC data) can be used.

For example, different chromatography modeling workflows are described in the literature in order to obtain chromatography model-specific property values of proteins. When working at elevated protein concentrations in the non-linear range of the isotherm, different models can affect the chromatogram in the same way. For example the position of the peak maximum changes in dependence on the shielding factor, v or Keq. For estimation of parameters in the linear range of the isotherm, Yamamoto equations can be applied as described for example, in M. Rüdt, F. Gillet, S. Heege, J. Hitzler, B. Kalbfuss, B. Guélat, "Combined Yamamoto approach for simultaneous estimation of adsorption isotherm and kinetic parameters in ion-exchange chromatography", Journal of Chromatography A, 1413 (2015) 68-76 and in S. Yamamoto, K. Nakanishi, R. Matsuno, T.

Kamikuno, "Ion-exchange chromatography of proteins—Prediction of Elution Curves and Operating Conditions", I. Theoredical Considerations, Biotechnology and Bioengineering, 25 (1983) 1465-1483.

According to embodiments, experiments in the linear range of the isotherm are evaluated with one or more of the following three methods: 1) Parameter estimation by curve fitting of chromatograms (T. Hahn, T. Huuk, V. Heuveline, J. Hubbuch, Simulating and Optimizing Preparative Protein Chromatography with ChromX, Journal of Chemical Education, 92 (2015) 1497-1502); 2) Logarithmic graphical evaluation using log(GH)/log(c(Na+)) plots described by Yamamoto et al. (T. Ishihara, T. Kadoya, H. Yoshida, T. Tamada, S. Yamamoto, Rational methods for predicting human monoclonal antibodies retention in protein A affinity chromatography and cation exchange chromatography: Structure-based chromatography design for monoclonal antibodies, Journal of Chromatography A, 1093 (2005) 126-138.) and 3) Non-logarithmic graphical evaluation of GH(c(Na+)) plots (M. Schmidt, M. Hafner, C. Frech, Modeling of salt and pH gradient elution in ion-exchange chromatography, Journal of Separation Science, 37 (2014) 5-13). If no good correlation is observed at this point, the chosen model might be not suited for the application.

The next step is the addition of experiments at high protein whereby the result of the evaluation of the linear gradient data can be used to improve parameter estimation. If chromatogram curve fitting results in a good correlation between the model and the experimental data, the parameter set can be tested by performing verification runs at important process parameter combinations not included in the calibration data set. If no satisfying model is found, either the model equations have to be extended or the dataset has to be reduced to a smaller design space. In the following, the obtaining of some of the model specific chemical properties of the proteins according to embodiments of the invention will be described.

According to some embodiments, Yamamoto evaluation was performed for obtaining model-specific protein properties. For example, the graphical log(GH)/log(c(Na+)) evaluation of the linear gradient elution experiments was performed as described elsewhere (M. Schmidt, M. Hafner, C. Frech, Modeling of salt and pH gradient elution in ion-exchange chromatography, Journal of Separation Science, 37 (2014) 5-13. T. Ishihara, T. Kadoya, H. Yoshida, T. Tamada, S. Yamamoto, Rational methods for predicting human monoclonal antibodies retention in protein A affinity chromatography and cation exchange chromatography: Structure-based chromatography design for monoclonal antibodies, Journal of Chromatography A, 1093 (2005) 126-138). The normalized gradient slope GH for salt gradients can be calculated as follows:

$$GH_{c(Na^+)} = \frac{c(Na^+)_{final} - c(Na^+)_{inital}}{V_G}(V_C(1 - \varepsilon_{col})\varepsilon_P k_D) \tag{F1}$$

$V_G$ is the gradient volume, $V_C$ the column volume, $\varepsilon_{col}$ the interstitial column porosity, $\varepsilon_p$ the bead porosity and $k_D$ the exclusion factor. $K_D$ was assumed to be 0.6 (F. Wittkopp, L. Peeck, M. Hafner, C. Frech, Modeling and simulation of protein elution in linear pH and salt gradients on weak, strong and mixed cation exchange resins applying an extended Donnan ion exchange model, J Chromatogr A, 1545 (2018) 32-47). The number of binding sites can be determined by plotting log(GH)/log(c(Na$^+$)) and subtracting 1 from the slope (M. Schmidt, M. Hafner, C. Frech, Modeling of salt and pH gradient elution in ion-exchange chromatography, Journal of Separation Science, 37 (2014) 5-13). The equilibrium constant can be calculated with the same graph for a monovalent salt:

$$K_{eq} = \frac{10^{-yintercept}}{\Lambda^{\nu}(\nu+1) + c(Na^+)_{initial}{}^{\nu+1}} \tag{F2}$$

The free Gibbs energies of the protein $\Delta G^0{}_P/RT$ and the salt $\Delta G^0{}_s/RT$ can be determined from the slope and the y-intercept by plotting $\ln(K_{eq})/\nu$ according to the following equation:

$$\ln(K_{eq}) = -\Delta G_P^0 + \nu(pH)\Delta G_s^0 \tag{F3}$$

All calculations were performed in Microsoft Excel applying the internal linear regression function of the software.

According to embodiments, in a further step, GH/c(Na+) curve fitting was performed. The GH/c(Na+) curve was performed according to previous publications by calculating the differential equation (S. Kluters, F. Wittkopp, M. Johnck, C. Frech, Application of linear pH gradients for the modeling of ion exchange chromatography: Separation of monoclonal antibody monomer from aggregates, J Sep Sci, 39 (2016) 663-675; and M. Schmidt, M. Hafner, C. Frech, Modeling of salt and pH gradient elution in ion-exchange chromatography, Journal of Separation Science, 37 (2014) 5-13):

$$\frac{\partial GH_{salt}}{\partial c_{SALT,elu}} = \frac{c_{PROT\_i}}{q_{PROT\_i}} = \left[ K_{eq,i}\left( \frac{\Lambda - \sum_{i=1}^{n}(\nu_i + \sigma_i)q_{prot,i}}{c_{SALT}} \right)^{\nu_i} \right]^{-1} \tag{1}$$

wherein $GH_{salt}$ is a normalized gradient slope for salt gradients, $c_{SALT}$ is the concentration of the free (unbound) salt ion in the mobile phase of the column, $c_{SALT,elu}$ is the concentration of the salt in the elution buffer at the elution peak maximum, $q_{PROT\_i}$ is the concentration of the protein i bound in the stationary phase, $K_{eq\_i}$ is the equilibrium constant (i.e., the molar concentration of a particular protein i in the stationary phase divided by the molar concentration of the protein i in the mobile phase), $\Lambda$ is the ligand density (defined as the number of ligands in mol per column volume), $\nu_i$ is the number of binding sites (i.e., the number of binding sites of protein i participating in protein binding to the stationary phase), $\sigma_i$ is the shielding factor.

The above-mentioned calculations can be performed, for example, in the Berkeley Madonna®, e.g. by applying the software's internal fourth order Runge-Kutta algorithm and a time stepping of 0.01 mol/L Na+. Parameter guess values were selected upon previously determined parameters of the Yamamoto evaluation and variated until no further improvement was achieved.

According to embodiments, in the next step, chromatogram curve fitting was performed. This step can be performed e.g. in ChromX from GoSilico. A lumped rate transport dispersive model was applied, e.g. with a Linear SUPG space discretization of 30 cells. Initial time stepping was set to 0.2 s using the IDAS function. For global optimization the ASA algorithm with the software standard values was used. For deterministic optimization, the IOPT algorithm was used. Fraction data was imported as percent of absolute UV signal measured by the ÄKTA system. Temporal correspondence of the experimental data and the simulation was confirmed by correlating the salt experimental and simulation data. Limits for parameters estimation can be selected upon previous results and adapted when the optimizing function calculated values close to the boundaries. Model parameters were determined using the software's Estimation function. Pool analytic measurements were considered using the Optimization function with the respective pooling criteria. The influence on dispersion by different Akta systems was considered by adding a continuous stirred tank reactor before the column with different lengths. Latin hypercube sampling was performed with a population size of 1000 using the Sampling function. All calculations can also be performed in other software packages e.g. CADET.

In other cases, the model-specific protein parameters may be obtained directly from literature and stored e.g. in a configuration file of the chromatography simulation software.

After having provided all input parameters to the chromatography simulation software, e.g. via a GUI and/or via a configuration file or via a further data source, the chromatography simulation software computes in step 108 an elution buffer salt concentration adapted to elute the first target protein from the chromatography column.

In particular, according to embodiments of the invention, the computing of the elution buffer salt concentration can comprise computing the amount and/or purity of the one or more target proteins as a function for each of a plurality of candidate elution buffer salt concentrations, outputting the amount and/or purity of the one or more target proteins computed for each of the candidate elution salt concentrations in association with the respective candidate elution salt concentration and receiving, from a user or from a software function, a selection of the one of the candidate elution salt concentration for which the amount and/or purity of the one or more target proteins best matches the desired amount(s) and/or purities of the one or more target proteins input in step 106.

The chromatography simulation software is configured to compute the salt concentration as a function of a set of parameter values comprising at least: a predefined pH value of the elution buffer; the dimension of the provided cation exchange chromatography column; the input amounts of the applied proteins (P1-P6); and chemical properties of the proteins of the applied protein solution. As mentioned above, these parameter values can be provided via a GUI and/or via a configuration file or via other data sources.

After having computed the elution salt concentration that is (best) suited for obtaining an elution target volume comprising the first and/or second target protein in the desired absolute or relative amount and/or purity, the chromatography simulation software computes in-step 110 the pooling borders of a target elution volume that comprises two one or more target proteins in the desired amount(s) and/or in the desired purity as a function of at least the computed salt concentration and the input desired amount of the first target protein. Preferably, the chromatography simulation program uses one or more chromatography models when computing the best suited elution salt concentration based on protein amounts and purities obtained for many different candidate elution salt concentrations and/or when computing the target elution volume based on the elution salt concentration obtained in step 108.

Next in step 112, a pump comprised in an automated or semi-automated chromatography system applies an elution buffer whose pH value is identical to the pH value having been input in the chromatography simulation software and whose salt concentration is identical to the salt concentration computed in step 108.

According to one example, an "elution buffer A" is prepared in accordance with the computed salt concentration, whereby the buffer consists of 0.04 mol/L Na-acetate.

According to another example, an "elution buffer B" is prepared in accordance with the computed salt concentration, whereby the buffer consists of a 1 mol/L Na-acetate solution. The buffers can be prepared e.g. with 30% acetic acid (Merck Chemicals GmbH) and Na-acetate*3H20 (Merck Chemicals GmbH) resulting in pH values of 5.30 and 5.70.

The chromatography is performed in step 114 by continuously applying the elution buffer on the column and pumping the elution buffer through the column at a rate that was used by the chromatography simulation software to predict the pooling borders. Often, the volume of the elution buffer that needs to be applied until the start pooling border is reached is many times the volume of the chromatography column.

Then in step 116, a human user or an automated or semi-automated chromatography system collects the computed target elution volume as a separate fraction using the pooling borders computed in step 110. For example, a robotic arm holding an empty container can be configured to move the container under the outlet of the column such that the container starts collecting the eluate leaving the column at the start pooling border of the computed target elution volume and to remove the container from the outlet such that the collection of the eluate stops when the stop-pooling border is reached. The eluate collected in the container is the target elution volume comprising the one or more target proteins in the desired amount and/or purity.

According to some embodiments, the steps 104-110 are performed before the protein solution is actually applied on the column. In this case, it is possible to perform one or more optional steps. For example, the column 230 can be equilibrated with the elution buffer that is to be used in step 112 until pH and conductivity readings stabilize before the protein solution is actually applied on the sample. For example, the equilibration of the column may require 3-5 column volumes of elution buffer that is applied for equilibration purposes before the actual protein solution is applied.

FIG. 2 shows a chromatography system comprising a computer system 200 with a chromatography simulation software 204 and a cation chromatography column 230. It being understood that the computer system 200 includes memory for storing the software 204, associated data, etc. and that the computer system includes processing circuitry (e.g., one or more central processing units) configured to execute the software 204 and cause the computer system 200 to perform the methods described herein. Stated another way, the computer system 200 executes the software 204 to perform the methods described herein. Still further, the computer systems 200 executes the software to cause the chromatography system to perform the methods described herein. In the embodiment depicted in FIG. 2, the chromatography system is used for selectively obtaining a first target protein P1 and a second target protein P2. The target proteins are contained in a protein solution 202 comprising additional proteins P3-P6 which are non-target proteins in the application scenario illustrated in this figure. Before the protein solution is applied on the column, the concentration of each protein P1-P6 in the protein solution 202 is determined. In addition, several chemical properties of the individual proteins P1-P6 are derived from literature or are determined experimentally.

The chromatography simulation program 204 comprises a GUI 202 enabling a user to specify, e.g. via input field 214, a desired optimization criterion, e.g. an amount and/or a desired purity of the first and second target proteins P1, P2 or a derivative value of the amount and purity. In addition, the GUI comprises one or more additional data entry fields 215, 216 enabling a user to specify the nature and amount of each of the proteins P2-P6 contained in the protein solution 202, to specify the dimensions of the column 230 and additional parameter values such as the pH of the elution buffer, some chemical properties of each of the proteins P1-P6, the type of predictive models to be used for simulating the chromatography, and the like.

The chromatography simulation software can comprise a plurality of predictive models 206-210 configured for modeling one or more aspects of the chromatography process. Some of the parameters used by the simulation software 204 or by the chromatography simulation models 206-210 can be specified in a configuration file 220.

The chromatography simulation software 204 is configured to predict an elution buffer salt concentration 222 that is best suited for obtaining the target proteins P1, P2 within a target elution volume at the desired amount and/or purity. For example, the simulation software 204 can be configured to simulate, for each of a plurality of different candidate elution buffer salt concentrations, the expected elution curves for each of the proteins contained in the protein solution which implicitly provide the amount and purity profiles of each of the proteins during the whole elution process. The simulation can be based on a combination of multiple different models respectively being descriptive of different aspects of a chromatography process. Based on these simulations, a user or a software function can select the one of the candidate elution buffer salt concentration that is best suited for eluting the target protein P1 in the desired amount and/or purity.

According to one embodiment, the computed elution salt concentration 222 is output via the GUI 212, 218 to a user and the user creates an elution buffer 226 having the pH that was input to the simulation software and that has the salt concentration 222 output by the software 204. In addition, the GUI can output the pooling borders 224 of the target elution volume predicted to comprise the target protein in the desired amount and/or purity.

The elution buffer 226 is particularly suited for separating the target proteins P1, P2 from all other proteins, because the elution buffer salt concentration was computed specifically for the amounts of each of the proteins P1-P6 applied to the column. Hence, the elution buffer is not a "standard"/"one fits all" elution buffer, but is rather an elution buffer specifically adapted to the type and amount of proteins contained in the protein solution. Applicant has observed that adapting the elution salt concentration to the nature and amounts of the proteins applied in each individual case to the column (which again may depend on various aspects of the cell culture extraction and pre-purification procedures) may greatly increase the ability of a chromatography column 232 separate different proteins.

The user first applies the protein solution 202 on the column 230 and then applies the elution buffer 226. The elution buffer 226 and the protein solution 202 seep through the column 230. Thereby, the molecules of the different proteins P1-P6 interact with the stationary phase 228 of the column 230 in dependence with their chemical properties. The interaction of the protein molecules with the stationary phase and also with the elution buffer determines their elution profile, i.e., the amount of the respective protein that leaves the column at a given time. By changing the containers 232, 234, 236 that are used for collecting the eluate leaving the outlet 238 of the column, different fractions 238, 240 of the eluate can be obtained. According to preferred embodiments, the exchange of containers is coordinates such that the target elution volume predicted to comprise the target proteins in the desired amount and/or purity is collected within the same container. This means, the pooling borders of the predicted target elution volume determine the time when a collection is placed below and removed from below the outlet of the column.

The volume of the protein solution is much smaller than the volume of the applied elution buffer and hence is neglected in many chromatography simulation models.

In some embodiments, the elution buffer 226 is in fact a series of two or more different elution buffers having the same pH value but different salt concentrations. These different elution buffers are also referred to as "elution steps". For example, the chromatography simulation software can be configured to compute the most suitable salt concentration for different elution steps.

FIG. 3 depicts a further chromatography system. The chromatography system depicted in FIG. 3 can be the same as the one depicted in FIG. 2, whereby the software 204 is used not for obtaining a single target protein in a desired amount, but rather for obtaining two target proteins P1, P2 in a desired ratio.

The components and features of the system depicted in FIG. 3 basically correspond to the components and features of the system depicted in FIG. 2. The explanations provided in respect to these features in the description of FIG. 2 will therefore not be repeated.

In contrast to the GUI depicted in FIG. 2, the GUI 212 generated by the simulation software 204 and depicted in FIG. 3 enables a user to specify via data entry field 304 a desired relative amount of two target proteins P1, P2. Optionally, the user may specify a required minimum purity level for each of the target proteins P1, P2. The computing of the elution buffer salt concentration 222 that is best suited for providing a target elution volume comprising the two target proteins in the desired ratio and, optionally, in the desired purity, comprises simulating a plurality of chromatography processes based on a plurality of different candidate elution buffer salt concentrations, determining the relative amount and optionally also the purity of the two target proteins in the target elution volume, and outputting the one of the candidate elution buffer salt concentrations that is best suited for providing a target elution volume comprising P1 and P2 in the desired relative amount and purity. each simulation can comprise predicting an elution profile for each of the proteins P1-P6 based on a given candidate elution buffer salt concentration, and then analyzing the elution profile of each of the proteins P1-P6 for determining pooling borders of a target elution volume whose protein content fulfills the user-defined requirements in respect to the relative target protein amount and purity.

Figure 4A:
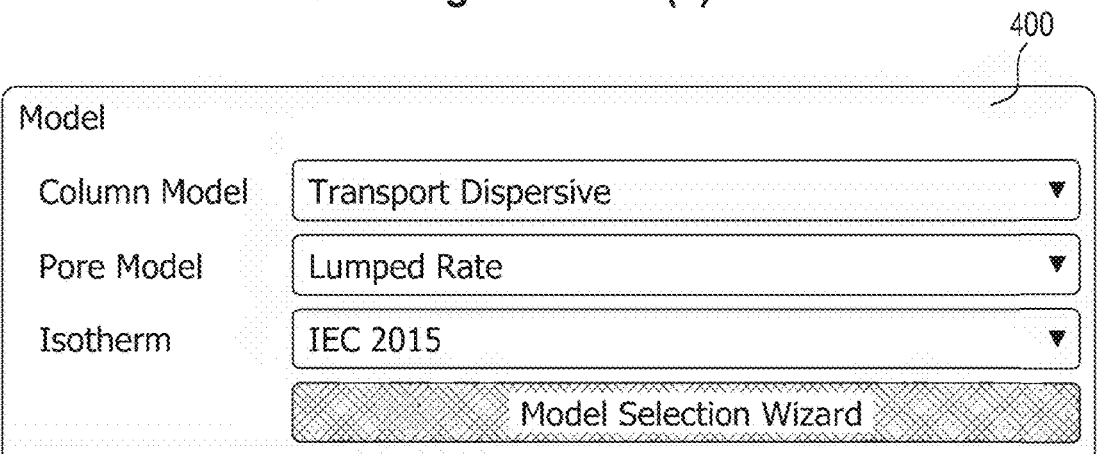
FIG. 4A depicts a GUI for selecting models to be used by a chromatography simulation software FIGS. 4B,C further illustrate the respective model types.
Figure 4B:
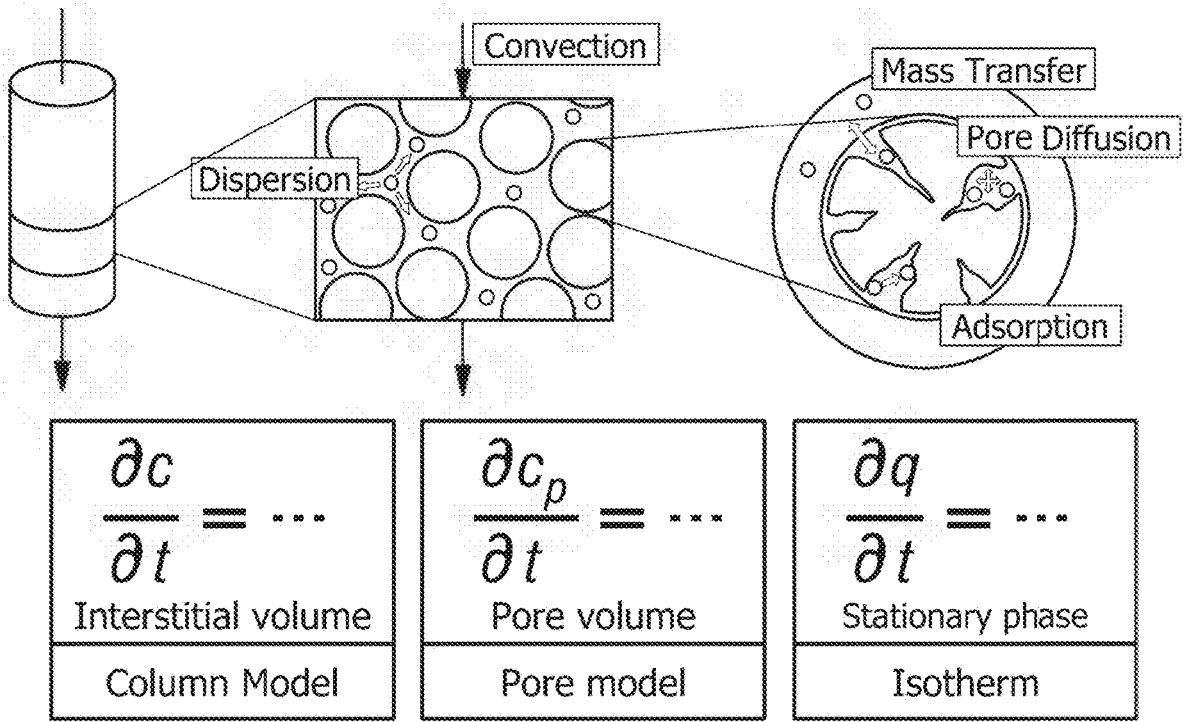
FIGS. 4D-E depicts GUIs for entering data in a chromatography simulation software.

FIG. 4A depicts GUI 400 enabling a user to select a plurality of different chromatography process simulation models for different aspects of the chromatography process. FIG. 4B illustrates the aspects of a chromatography process simulated by the respective model.

For example, the GUI enables the user to select the model "transport dispersive" from a plurality of alternative column models. A "column model" as used herein is a model being descriptive of the interrelation of the concentration of each of the proteins, the salt concentration and the pH value in the elution buffer in the interstitial volume of the column.

The GUI 400 further enables the user to select the model "LumpedRate" from a plurality of alternative pore models. A "pore model" as used herein is descriptive of the interrelation of the concentration of each of the proteins, the salt concentration and the pH value in the elution buffer in the pore volume of the stationary phase 228 of the column.

The GUI 400 further enables the user to select the model "IEC 2015" from a plurality of alternative reaction models, also referred to as "Isotherm models". A "reaction model" as used herein is descriptive of the interrelation of the concentration of each of the proteins in the stationary phase 228, the elution buffer salt concentration and at least some of the chemical properties of each of the proteins in the protein solution.

The different models can be derived from literature and/or can be based on protein specific model parameters which are determined experimentally.

FIG. 4C illustrates the mathematical concepts behind each of the model types that can be selected via GUI 400 according to one embodiment of the invention in greater detail. However, alternative models have been published and it is likely that at least some of the models depicted in FIG. 4B may be adapted and improved in the future. Hence, the invention is not limited to any specific model or mathematical formula described herein for illustrative purposes.

Figure 4D:
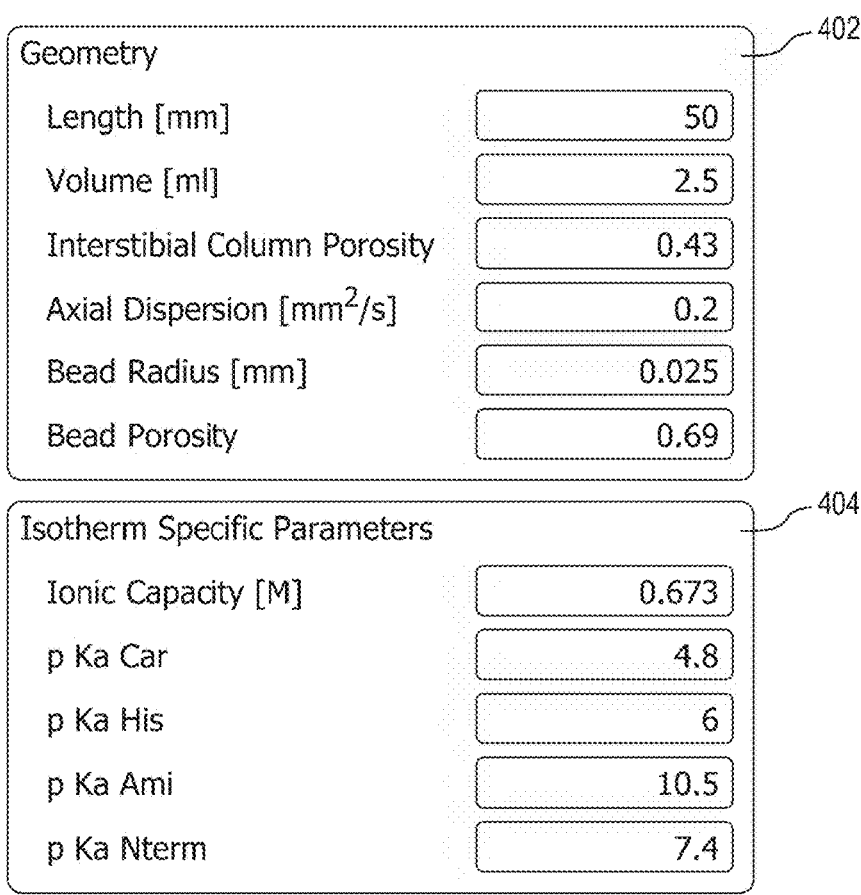

FIG. 4D depicts a graphical user interface 402 generated by the chromatography simulation software 204 and enabling a user to specify details of the chromatography column 230 and the stationary phase 228 contained therein. For example, the user can specify the length and volume of the column 230 as well as the interstitial column porosity, the axial dispersion, the bead radius and the bead porosity of the stationary phase 228. A further graphical user interface 404 generated by the chromatography simulation software 204 enables a user to specify model-specific chemical properties, e.g. the ionic capacity of the stationary phase (that corresponds to the ligand density), the acid dissociation constants of a carboxyl group, of a histidine group, of an amino group, etc. The data entry fields of the GUI may depend on the type of model selected by the user via GUI 400.

Figure 4E:
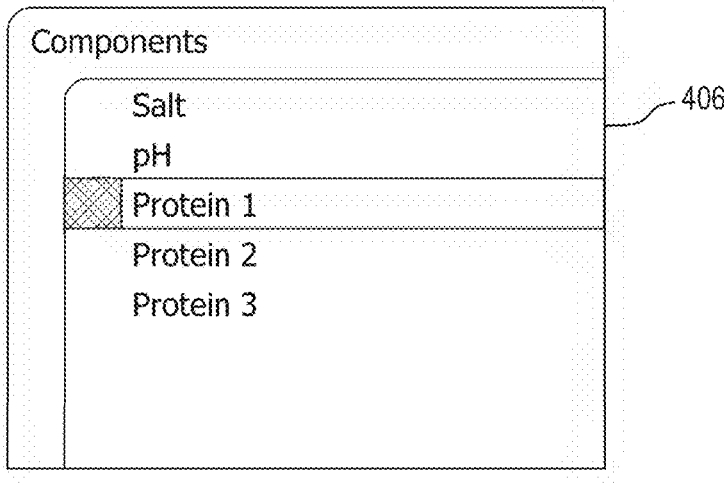

FIG. 4E depicts a GUI 406 enabling a user to specify the type of salt of the elution buffer, the pH value of the elution buffer, the number and types of proteins comprised in the protein solution, as well as one or more protein specific desired absolute or relative amounts, desired purity levels and model-specific or model-independent chemical property values.

Figure 5A:
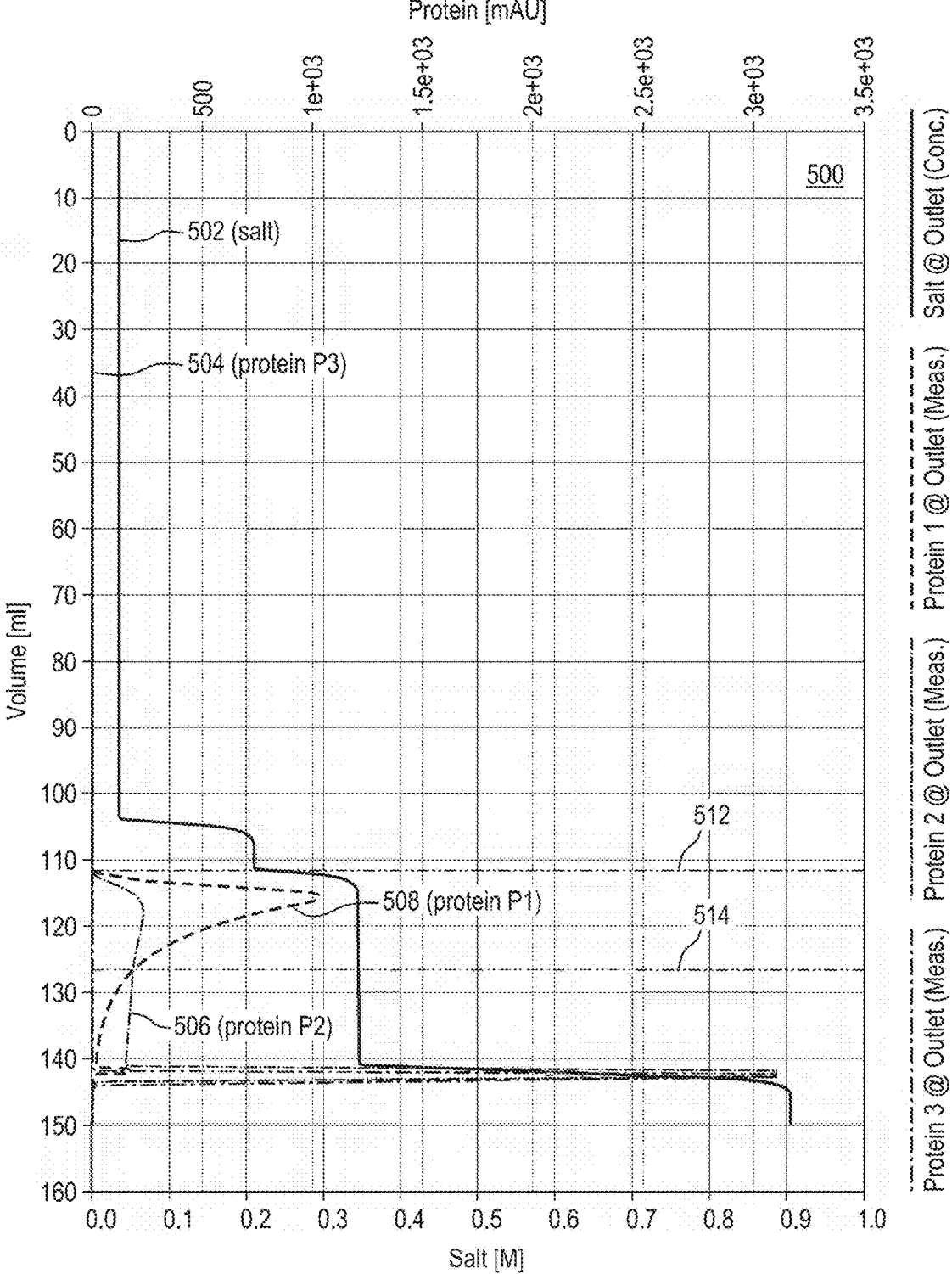
FIG. 5A is an elution plot obtained for a first protein solution.

FIG. 5A is an elution plot 500 showing the simulated elution profiles of multiple proteins P1, P2 and P3 comprised in a protein solution applied on a column. The proteins P1, P2 and P3 can be, for example, the proteins P1, P2 and P3 described in greater detail with reference to FIGS. 7A-7D.

Protein P1 is provided as a target protein and a user has specified that P1 should be obtained in a predefined concentration and a predefined purity. The other proteins P2 and P3 are non-target proteins. This means, P2 and P3 are considered as undesired contaminants whose concentration should be as low as possible to ensure sufficient purity of P1.

The plot 500 comprises a curve 502 that is indicative of the candidate elution salt concentration used in the simulation that provides the plot 500. As can be derived from the plot, the candidate elution buffer is in fact a series of multiple different candidate elution buffers with different salt concentrations ("elution steps"). As soon as the elution buffer salt concentration rises above 0.35 mol/l, the target protein P1 as well as the non-target protein P2 start to detach from the column and are observable in the eluate. this can be derived from the respective elution profiles 508 for protein P1 and 506 for protein P2. Once the salt concentration rises above 0.9 mol/l, also P3 is eluted as derivable from elution profile 504.

The chromatography simulation software is configured to simulate (predict) the elution profiles 504-508 for each of the candidate elution salt concentrations in the respective steps and for determining pooling borders which include an elution volume whose protein content fulfills the user-defined requirements in respect to the target protein amount and purity. The determined pooling borders are indicated by the dotted lines 512, 514. The two lines define a target elution volume that comprises the peak of protein P1. The target elution volume also comprises some amount of protein P2. However, by stopping the collection of the eluate at pooling border 514, it can be ensured that the purity of P1 in the target elution volume meets the user-defined purity requirement, because after this point an increasing relative amount of the non-target protein P2 would be contained in the target elution volume.

The plot depicted in FIG. 5A was described with reference to an optimization criterion that is directed on a single target protein P1. However, in other use-case scenarios, also the protein P2 can be considered as target protein (see for example FIG. 6A) and the optimization criterion can be a criterion related to the amount and/or purity of two target proteins P1, P2 while only P3 is considered as contaminant. In this case, the pooling borders would be adapted to the new optimization criterion.

Figures 5B, 5C:
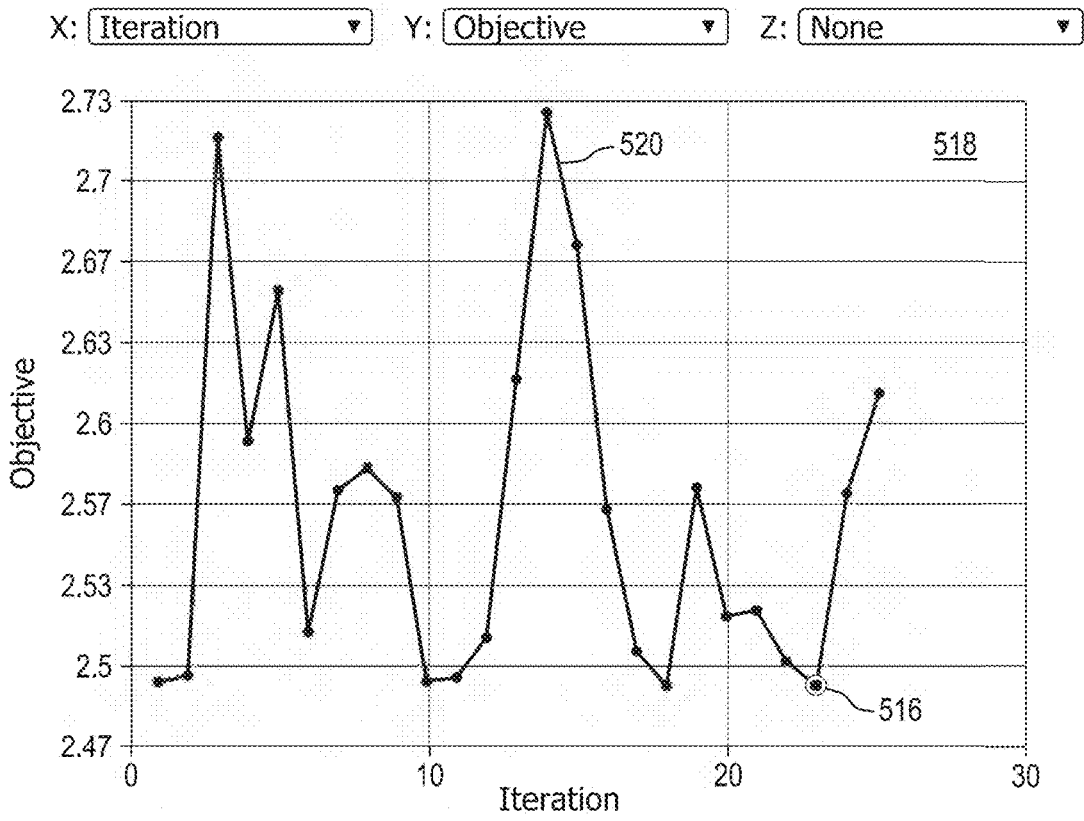
FIG. 5B depicts predicted results for the yield and purity and for a combined purity-yield-objective parameter of a target protein in the first protein solution given multiple different candidate elution salt concentrations.
FIG. 5C depicts a plot with predicted results for the combined purity/yield-objective parameter of a target protein in the first protein solution given multiple different candidate elution salt concentrations.

FIG. 5B depicts predicted results for the yield and purity and for a combined purity-yield-objective parameter of the target protein P1 in the first protein solution given multiple different candidate elution salt concentrations. The "purity" indicates a predicted purity of P1 in the target elution volume given the candidate salt concentration. The "yield" indicates a predicted amount of the target protein P1 in the target elution volume given the candidate salt concentration. The "objective" is an aggregate value derived from a combination of the predicted amount and purity of P1. For example, the "objective" depicted in FIG. 5B is a "composite objective" computed as follows:

Single Objective SO=F*(Objective)Power+A, wherein F ("factor") is a numerical value, POWER is a numerical value, and A ("addend") is also a numerical value.

Composite objectives can be generated by combining single objectives by multiplication or addition.

For example, the following parameters can be chosen: POWER=1, F=1 and A=0. However, each of these parameters may also have different values.

The objective SO1 computed in iteration 10 for elution buffer salt concentration 0.342544 is the predicted purity of the protein P1 in the target elution volume, whereby the elution pool volume starts at 135 mL and ends at 147 mL. The predicted purity SO1 has the value 0.751832. The objective SO2 is the yield of protein P1 computed in iteration 10 for elution buffer salt concentration 0.342544. The predicted yield SO2 has the value 0.836734.

A composite objective CO1 can be computed by aggregating SO1 and SO2, e.g. computing SO1+SO2. According to another example, a composite objective CO2 is computed as SO1*SO2.

The results are presented in the form of a table 510. The first column of the table ("iteration") comprises an identifier of a candidate elution buffer salt concentration or a set of candidate elution buffer salt concentrations (for the multiple steps) used as a basis for a respective chromatography simulation. A further column ("salt concentration") indicates the candidate elution buffer salt concentration to be used in a particular elution step. A further column ("purity protein 1") indicates a purity value predicted for the given candidate elution buffer salt concentration. A further column ("yield protein 1") indicates the amount (e.g. concentration) of protein P1 predicted for the given candidate elution buffer salt concentration. A further column ("objective") indicates an objective that is to be optimized (here: minimized) and that is computed as a function of the predicted purity and the predicted yield of the target protein P1.

Each row in the table 510 corresponds to one candidate elution buffer salt concentration and a respective prediction. The rows in table 510 are sorted in accordance to the objective value and the row having the optimum (here: minimum) objective and hence having the highest purity and yield appears as the first row in the table. In the example depicted in this figure, a numerical value for "purity" or "yield" as low as possible means that the purity or yield are as high as possible. This implies that the candidate elution buffer salt concentration 0.345 of the simulation with "iteration" number 23 is considered to be the optimum salt concentration for the given protein solution. As a consequence, the elution buffer that is actually to be used for the "real" elution is chosen such that it has the salt concentration of 0.345. There are also simulations in which a single value is higher, e.g. iteration 10. Here the purity is higher than in iteration 23, but the yield is lower. The best compromise between Purity and Yield (Pareto principle) is iteration 23.

FIG. 5C depicts a plot 518 with predicted results for the combined purity/yield-objective parameter of a target protein in the first protein solution given multiple different candidate elution salt concentrations. The curve 520 represents the purity/yield derived objective described with reference to FIG. 5B. Hence, the plot 518 of FIG. 5C illustrates the purity-yield objective obtained based on a plurality of different candidate elution buffer salt concentrations and respective simulations in the form of a curve rather than a column of a table 510. The data point 516 indicates that the minimum of this objective is obtained at iteration 23 and that the candidate elution buffer salt concentration used for this particular simulation #23 should be used as the actual elution buffer salt concentration for obtaining the target elution volume. The elution buffer salt concentration of the elution buffer step corresponding to the elution target volume delimited by pooling borders 512, 514 in plot 5A corresponds to the optimum salt concentration predicted in the simulation with the number #23.

Figure 6A:
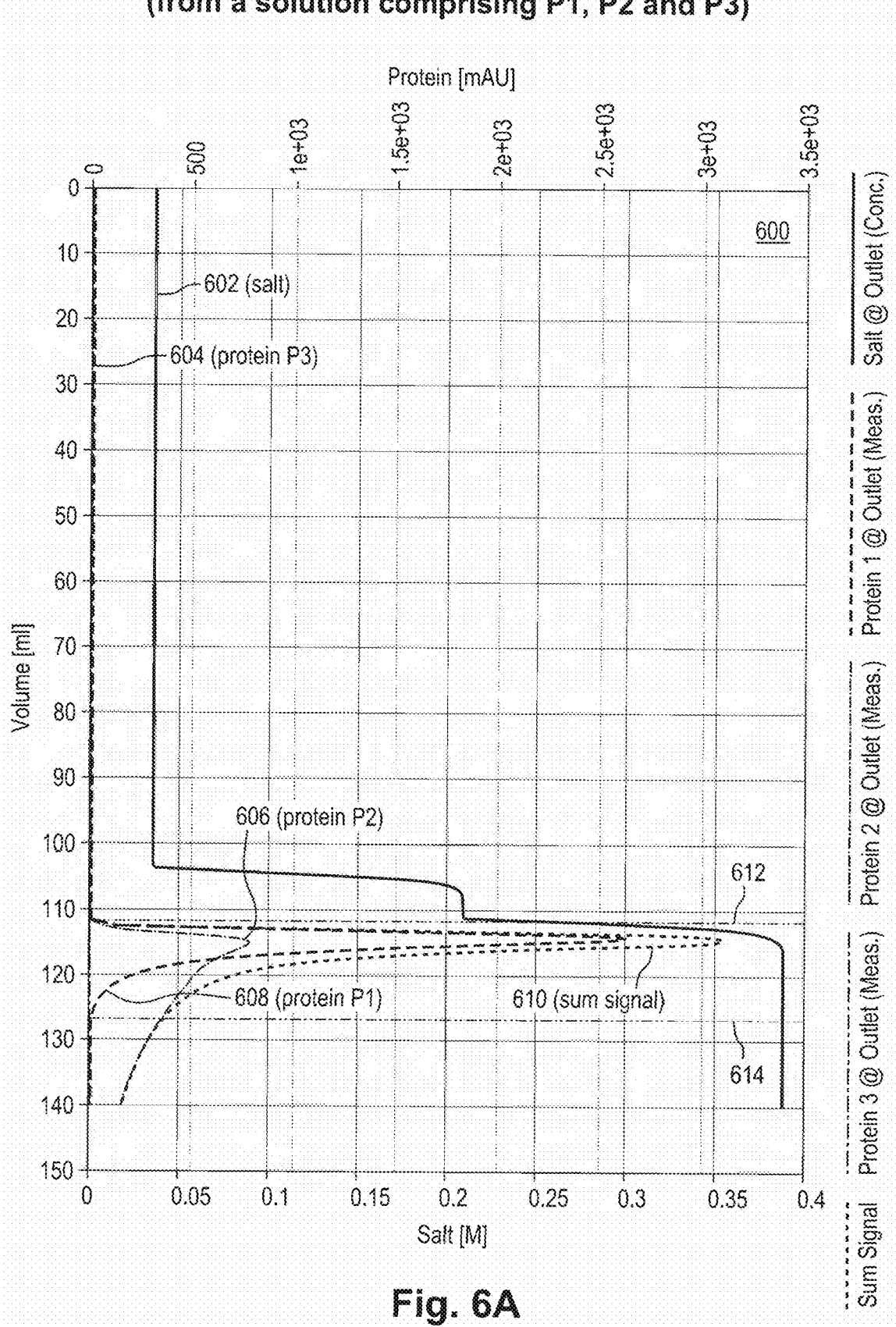
FIG. 6A is an elution plot obtained for a second protein solution.

FIG. 6A is an elution plot 600 obtained for a second protein solution. The second protein solution also comprises three proteins P1, P2 and P3. The proteins P1, P2 and P3 can be, for example, the proteins P1, P2 and P3 described in greater detail with reference to FIGS. 7A-7D.

In contrast to the situation described in FIG. 5A, both proteins P1 and P2 are considered to be target proteins. A user specifies via a graphical user interface that he or she is interested in obtaining proteins P1 and P2 in a ratio of 55:45. In addition, the obtained target elution volume should be as pure as possible, meaning that the target elution volume should comprise as little as possible of P3 and any other protein.

The simulated elution profile of protein P1 is depicted as curve 608, the simulated elution profile of protein P2 is depicted as curve 606, the simulated elution profile of protein P3 is depicted as curve 604, and the elution buffer salt concentration steps are depicted as curve 602. A simulation of the amounts and purities of the two target proteins P1 and P2 and of amount-and-purity derived objectives for each of a plurality of different candidate elution buffer concentrations reveals an optimum elution buffer salt concentration for each of the multiple steps and reveals pooling borders 612, 614 defining a target elution volume that comprises the first and second target proteins P1, P2 in the desired relative amount and fulfilling the specified purity requirements. In addition, the plot 600 comprises a simulated sum signal 610 being indicative of the total amount of proteins that can be used for comparing the predicted protein peaks with a total protein peak obtained empirically during the elution process.

Figures 6B, 6C:
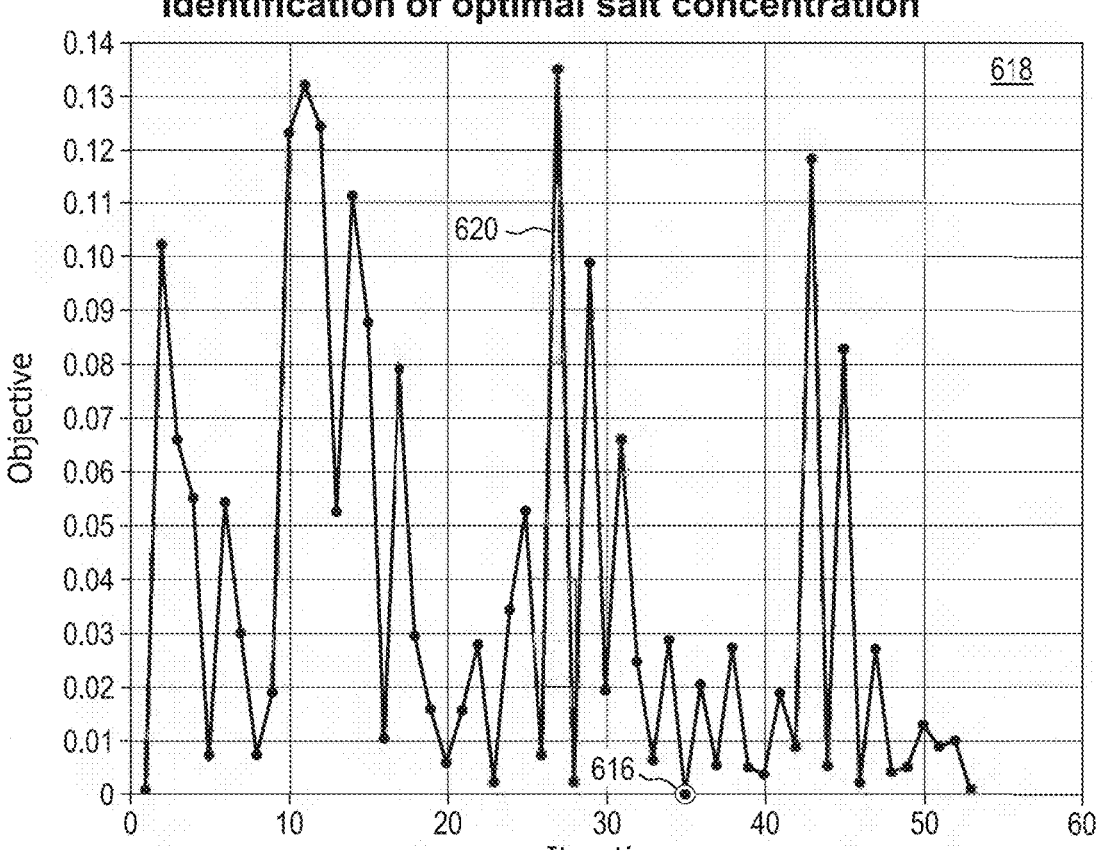
FIG. 6B depicts predicted results for the yield and purity and for a combined purity-yield-objective parameter of a first and a second target protein in the second protein solution given multiple different candidate elution salt concentrations.
FIG. 6C depicts a plot with predicted results for the combined purity/yield-objective parameter of a first and a second target protein in the second protein solution given multiple different candidate elution salt concentrations.

FIG. 6B depicts predicted results for the yield and purity and for a combined purity-yield-objective parameter of the target proteins P1 and P2 in the second protein solution given multiple different candidate elution salt concentrations. The "purity" indicates purity of the respective target protein P1, P2 in the target elution volume predicted for each of the candidate elution buffer salt concentrations.

The results are presented in the form of a table 617. The first column of the table ("iteration") comprises an identifier of a candidate elution buffer salt concentration or a set of candidate elution buffer salt concentrations (for the multiple steps) used as a basis for a respective chromatography simulation. A further column ("salt concentration") indicates the candidate elution buffer salt concentration to be used in a particular elution step. Further columns ("purity protein 1", "purity protein 2") indicate a purity value predicted for each of the proteins P1, P2 for the given candidate elution buffer salt concentration. A further column ("objective") indicates an objective that is to be optimized (here: minimized) and that is computed as a function of the predicted purities and the predicted relative amounts of the target proteins P1 and P2.

The "objective" (also referred to as "composite objective") can be, for example, an aggregate value derived from a combination of the predicted relative amount of P1 and P2 and of the desired purity levels of P1 and P2. For example, the "objective" CO can be computed from two single objectives SO1, SO2 by adding or multiplying the two single objectives. For example, CO can be computed as CO=SO1+ SO2 or as CO=SO1*SO2.

Thereby, SO1 is the purity of P1 in the target elution volume predicted for a given candidate elution buffer salt concentration, e.g., 1:0.55, whereby the elution target volume has been predicted to start at 112 mL and end at 127 mL. SO2 is 2:0.45 is the desired purity of P2 in the elution target volume, whereby the elution target volume has been predicted to start at 112 mL and end at 127 mL.

Optionally, an error between the computed objective CO and a target value can be calculated using the "reference comparison" cost function which calculates a pointwise squared deviation between objective and target value.

Each row in the table 617 corresponds to one candidate elution buffer salt concentration and a respective prediction. The rows in table 617 are sorted in accordance to the objective value and the row having the optimum (here: minimum) objective and hence having the highest purity and best matching P1:P2 ratio appears as the first row in the table. A value of the "objective" parameter that is as small as possible means that the difference between the single objectives and the corresponding target values is as small as possible. This implies that the candidate elution buffer salt concentration 0.388 of the simulation with "iteration" number 35 is considered to be the optimum salt concentration for the given protein solution. As a consequence, the elution buffer that is actually to be used for the "real" elution is chosen such that it has the salt concentration of 0.388.

FIG. 6C depicts a plot 618 with predicted results for the combined purity/yield-objective parameter of a target protein in the first protein solution given multiple different candidate elution salt concentrations. The curve 620 represents the purity/yield derived objective described with reference to FIG. 6B. Hence, the plot 618 of FIG. 6C illustrates the purity-yield objective obtained based on a plurality of different candidate elution buffer salt concentrations and respective simulations in the form of a curve rather than a column of a table 617. The data point 616 indicates that the minimum of this objective is obtained at iteration 35 and that the candidate elution buffer salt concentration used for this particular simulation #35 should be used as the actual elution buffer salt concentration. The elution buffer salt concentration of the elution buffer step corresponding to the elution target volume delimited by pooling borders 612, 614 in plot 6A corresponds to the optimum salt concentration predicted in the simulation with the number #35.

FIG. 6D depicts a comparison of a predicted and a measured protein ratio of P1 and P2 obtained for the second protein solution. The predicted concentration of protein P1 in the target elution volume delimited by pooling borders 612, 614 is predicted to be 51% based on a candidate elution buffer concentration of 0.388 mol/liter used in simulation #35. The empirically measured concentration of P1 in the target elution volume when an elution is performed with an elution buffer having a salt concentration of 0.388 mol/liter is 56%. Likewise, the predicted concentration of protein P2 in the target elution volume is 49%. The empirically measured concentration of P2 in the target elution volume is 44%. Hence, the accuracy of the predicted concentrations in a target elution volume defined by the predicted pooling borders is very high.

Figure 6E:
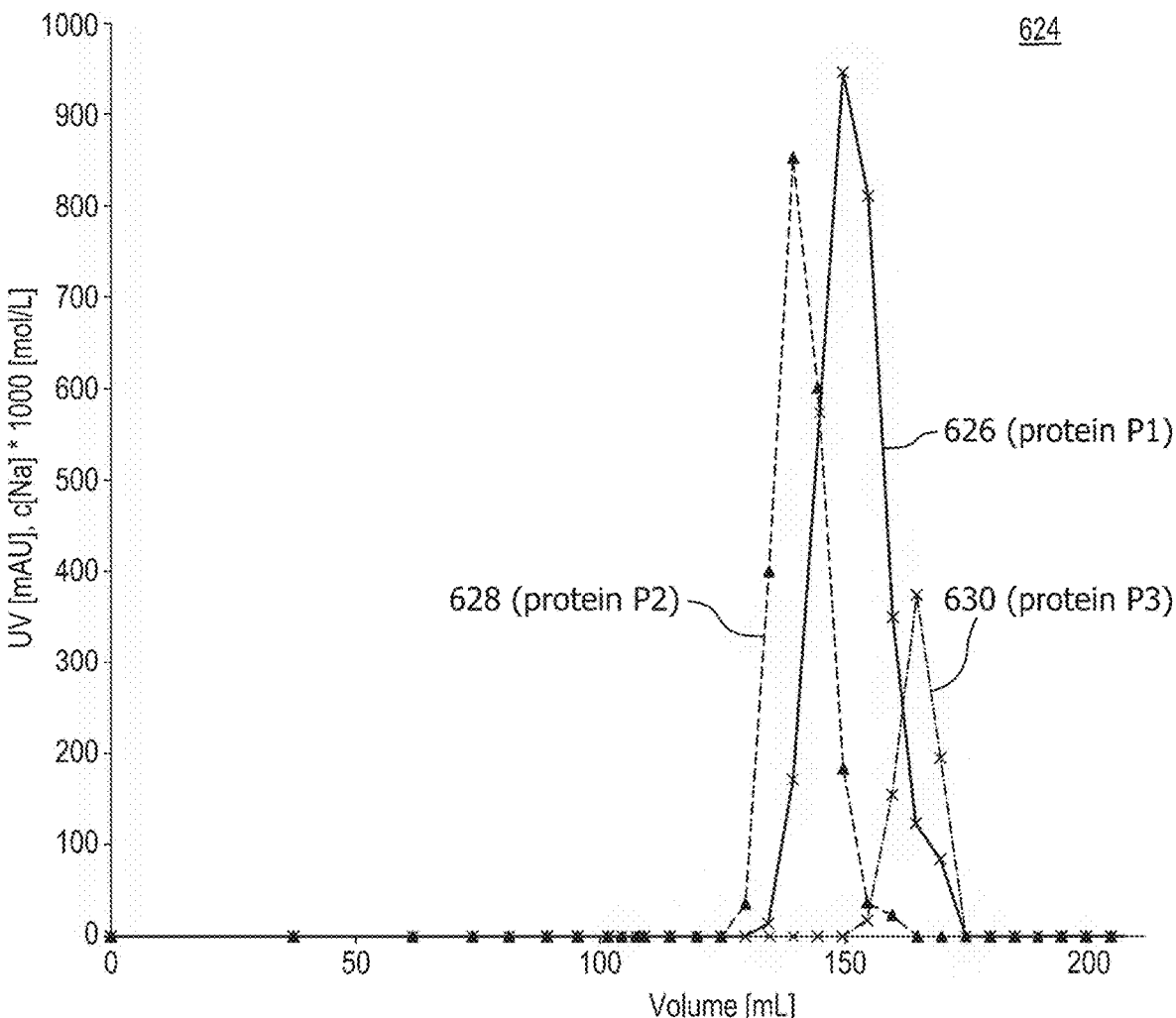
FIG. 6E depicts the resolution of proteins P1 and P2.

FIG. 6E depicts the empirically obtained resolution of proteins P1, P2 and P3. The plot 624 illustrates the optical peaks 626, 628, 630 induced by the elution of the respective proteins P1, P2, P3. As can be inferred from the plot, the peaks of P1 and P2 strongly overlap. The resolution R for the two proteins P1, P2 in a gradient of 40 column volumes at a protein load of 45 g/liter was observed to be about 0.43, i.e., very low. Embodiments of the invention may be used for obtaining two or more proteins in a desired ratio even in case these proteins have a low resolution value and without the need to separate the two proteins first and then re-combining the proteins in the desired ratio.

FIG. 7 depicts an example of two target proteins P1, P2 and a further protein P3 that is considered to be an undesired contamination.

Figure 7A:
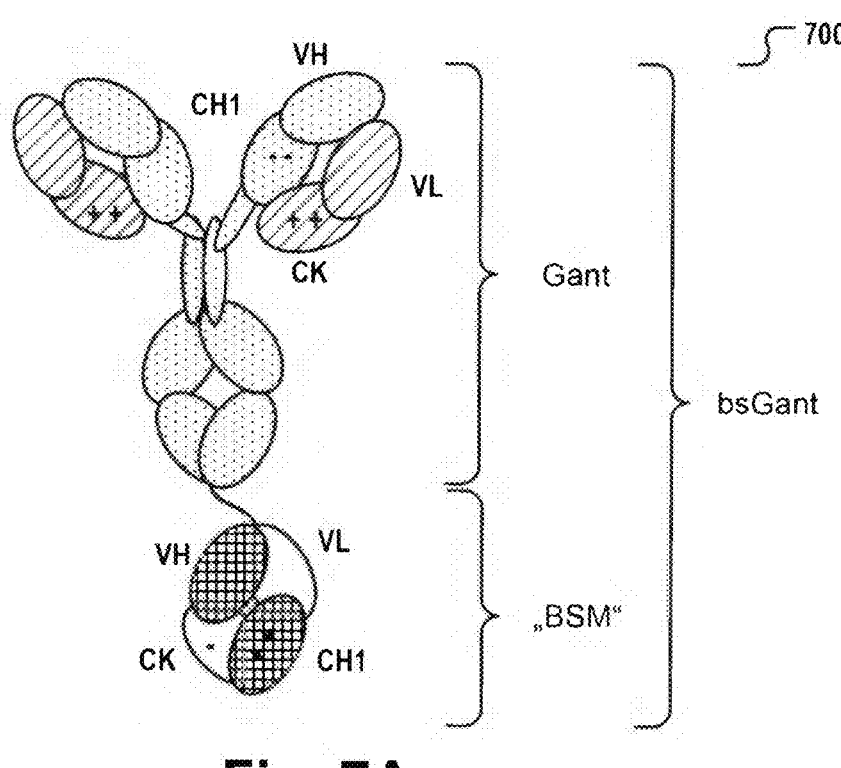
FIG. 7A-7D depicts an example of two target proteins P1, P2 and a further protein P3.

FIG. 7A shows an illustration of a protein 700 "bsGant" consisting of a brain shuttle molecule referred to as "BSM" that is linked to an antibody referred to herein as "Gant". A brain shuttle molecule is a molecule that is able to increase penetration of large molecules such as antibodies into the brain. Access of large molecules to the brain is restricted by the blood brain barrier (BBB), a gatekeeper between the blood and the brain tissue that carefully filters which molecules can enter the brain. Some antibodies engineered by the applicant are able to cross the blood brain barrier by binding to one of the protein receptors located on its surface. A brain shuttle molecule can potentially transport one or more therapeutic molecules into the brain, regardless of their intrinsic ability to cross the blood brain barrier. The bsGant protein is described in detail in the international patent application WO 2017/055540 which is incorporated herein by reference in its entirety.

The "bsGant" antibody is a monomeric Immunoglobulin G (IgG) Fc-fusion protein. The cell culture used for producing the "bsGant" antibody produces this antibody in three different variants differing in their extent of Fab glycosylation. The Fab glycosylation is not complete, leading to a mixture of non-glycosylated, mono-glycosylated and di-glycosylated antibodies.

According to embodiments, the one or more target proteins are different glycoforms of a monomeric bsGant protein (as defined above).

According to one example, one or more target proteins are different glycoforms of the bsGant "antibody 0015" described in the patent application WO 2017/055540. This antibody is a bispecific antibody comprising a light chain that has the amino acid sequence of SEQ ID NO: 01, a heavy chain that has the amino acid sequence of SEQ ID NO: 02, a light chain that has the amino acid sequence of SEQ ID NO: 03, and an antibody Fab fragment comprising the amino acid sequences of SEQ ID NO: 04 disclosed in WO 2017/055540. SEQ ID NO: 01 relates to a 215 aa residue polypeptide corresponding to the not-domain exchanged light chain of the N-terminal fabs, SEQ ID NO: 02 is a 455 aa residue polypeptide corresponding to the two heavy chains, SEQ ID NO: 03 is a 215 aa residue polypeptide corresponding to the domain exchanged light chain of the additional C-terminal fab fragment, and SEQ ID NO: 04 is a 229 aa residue fragment corresponding to the domain exchanged heavy chain of the additional C-terminal fab fragment.

Figures 7B, 7C, 7D:
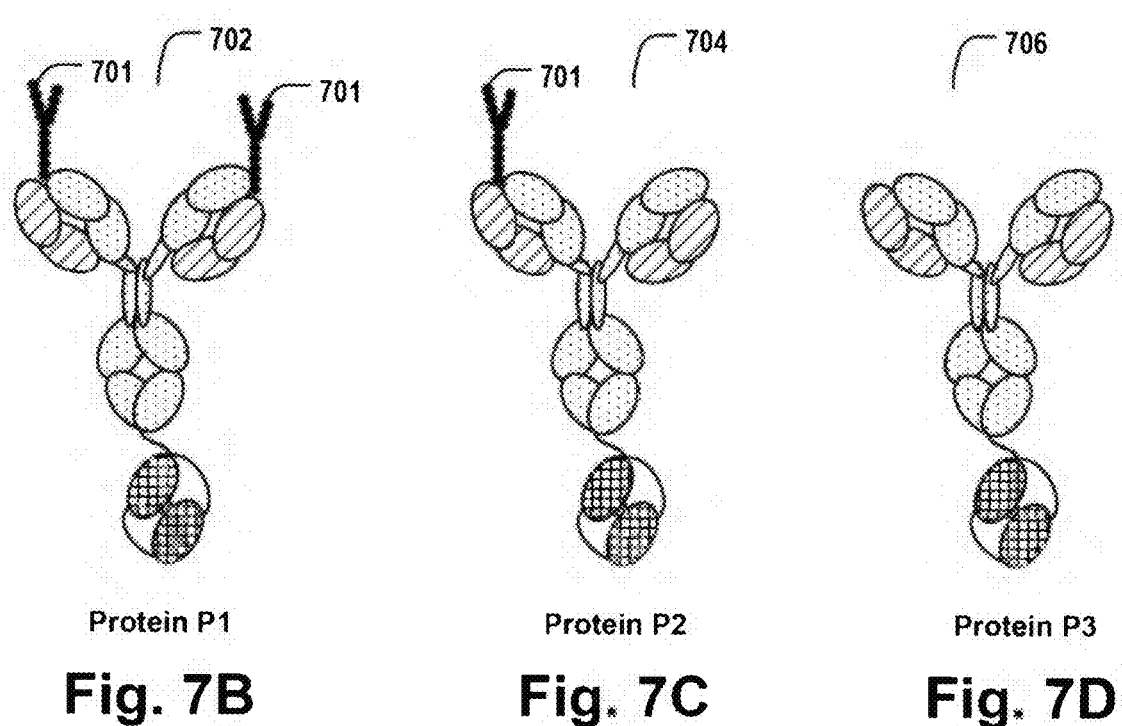

FIG. 7B shows the di-glycosylated antibody variant, also referred herein as "Protein P1".

FIG. 7C shows the mono-glycosylated antibody variant, also referred herein as "Protein P2".

FIG. 7D shows the non-glycosylated antibody variant, also referred herein as "Protein P3".

The close elution conditions of the three variants impose a particular challenge on the chromatography protocol used for separating and/or further purifying desired antibody variants.

Differences in the glycosylation pattern in the Fc-region of an antibody can lead to differences in conformation, pharmacokinetics as well as binding characteristics. Glycosylations of the Fab-region can influence ligand binding strength and tissue penetration. Therefore, glycosylation pattern is of special interest for a plurality of antibodies used in the medical domain. The glycosylation pattern may depend on the expression vector, cell line, cell culture mode as well as cell culture conditions, the purification process and other factors. As glycosylation variants may differ only slightly in the charge, the separation using ion exchange resins is possible but elution conditions have to be optimized.

Applicant has observed that the protein load density applied on a chromatography column is a further critical process parameter influencing the product pool composition. Embodiments of the invention may allow obtaining a desired ratio of antibody variants, e.g. a ratio of P1:P2 of 55:45, that is pharmaceutically particularly effective.

The challenge of separating a protein solution comprising the three proteins P1, P2 and P3 is that the product pool ("target elution volume") should contain a ratio of P1 to P2 of about 55%:45%. The yield of this separation is limited because of this relative amount criterion as the protein solution contains more than 50% of P2 (see Table 1). Protein P3 in this case is a product-specific impurity, namely the protein 700 protein without glycosylation.

Applicant has observed that the relative and absolute amounts of the proteins P1, P2 and P3 in the protein solution to be applied on the column may vary significantly from case to case and that this may impose a further challenge as a chromatography protocol that worked well for a particular protein preparation may fail to separate the proteins on a different preparation of these three protein variants.

For example, a protein solution comprising selectively the three proteins P1, P2 and P3 can be obtained by harvesting a cell culture genetically engineered to produce the protein 700 in the three glycosylation variants. All glycoforms were captured on a Protein A resin which was equilibrated before loading. The load density of the raw protein extract was 23 g protein per liter resin. The antibody was eluted and after a viral inactivation step the pH of the eluate was increased again and the solution was incubated overnight at 4° C. and filtrated over a 0.2 μm sterile filter. The filtrated Protein A eluate was used as the load material to a mixed mode chromatography resin. To remove protein impurities, the mixed mode chromatography resin was used. The column was equilibrated before loading. The load density was 25 g protein per liter resin and the flow rate 150 cm per hour. Afterwards the pH of the flow through eluate was decreased and the pool was filtrated over a 0.2 μm sterile filter.

The approach was repeated multiple times on six different cell culture extracts and the respectively obtained protein solutions to be applied on a cation column are summarized in "table 1" below:

| | Variant P1 [%] | Variant P2 [%] | Variant P3 [%] |
|---|---|---|---|
| Protein solution 1 | 36.2 | 50.8 | 13.0 |
| Protein solution 2 | 38.5 | 52.0 | 9.5 |
| Protein solution 3 | 34.2 | 52.5 | 13.3 |
| Protein solution 4 | 98.0 | 2.0 | 0.0 |
| Protein solution 5 | 2.4 | 97.6 | 0.0 |
| Protein solution 6 | 0.0 | 3.5 | 96.5 |

To isolate the single glycosylation variants, the PorosXS pool was diluted with water and reprocessed using a PorosXS resin in bind and elute mode at high protein load density. The column was equilibrated with 376 mM sodium acetate pH 5.5 and the load density was 80 g per liter resin. The flow through was fractionated and analyzed. The fractions at the beginning of the flow through contained variant 1 with a purity of 98.0% (protein solution 4). To eluate the variant 2 and 3 a gradient from 376 mM sodium acetate pH 5.5 to 616 mM sodium acetate pH 5.5 in 6.25 CV was used. The elution peaks contained variant 2 with a purity of 97.6% (protein solution 5) and variant 3 with a purity of 96.5% (protein solution 6).

Glycosylation variant analysis was performed by injecting 100 μg sample on an analytic cation exchange chromatography column (Mono S 5/50 GL, GE Healthcare) with a salt gradient elution at pH 5.3 at 1 ml/min flow velocity. Previous peak identification was done by mass spectrometry.

The system and resin parameters required for mechanistic modeling of various model parameters of the models 206-

210 were determined by pulse experiments with different tracers like described in A. Osberghaus, S. Hepbildikler, S. Nath, M. Haindl, E. von Lieres, J. Hubbuch, Determination of parameters for the steric mass action model—a comparison between two approaches, Journal of Chromatography A, 1233 (2012) 54-65. A latin hypercube sampling of size 1000 was performed to study the impact of process parameters (pH value, load composition, salt concentration of the elution step) on the impurity profile in the elution pool. For varying load density, the injection volume was changed. The simulations were performed with 5 second time steps, 30 axial cells, 5 cm column length at a flow rate of 300 cm/h using ChromX. For each in silico experiment impurity profiles and elution profiles of the individual proteins in the elution pool were calculated using a pooling decision with fixed volume. The results were analyzed in MATLAB using linear regression analysis with impurity pool concentration as dependent and process parameters as independent variables.

Figure 8A:
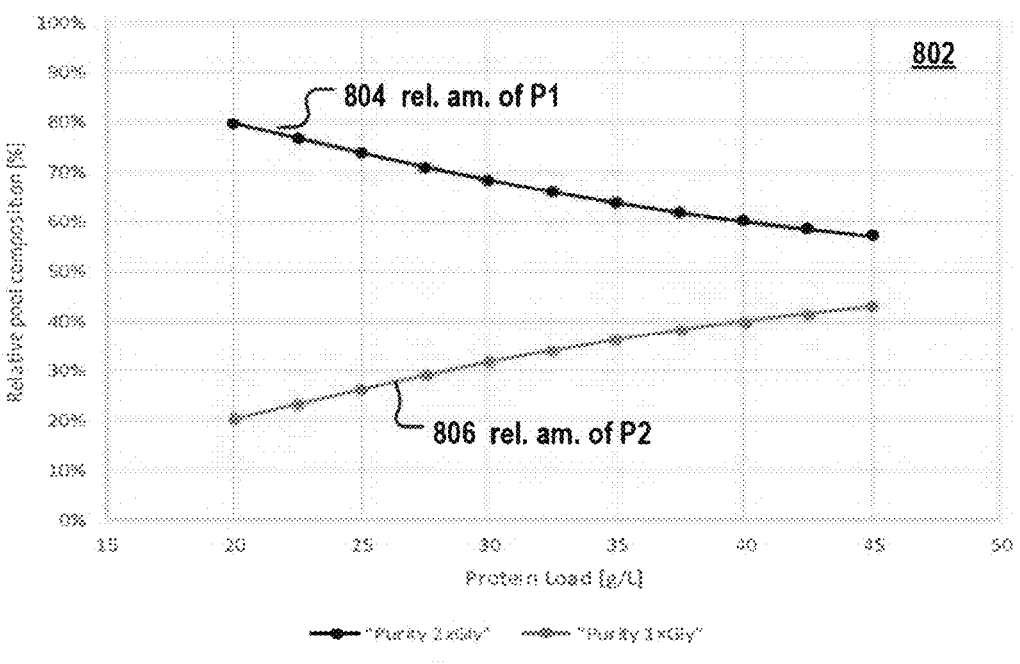
FIG. 8A is a plot illustrating the impact of protein load on the relative pool composition.

FIG. 8A shows a plot 802 illustrating the impact of protein load on the relative protein composition in the elution target volume. Assuming an elution buffer salt concentration of 40%, the relative amount of protein P1 in the eluate at different protein loads is illustrated in curve 802. The relative amount of protein P2 in the eluate is illustrated in curve 804.

Figure 8B:
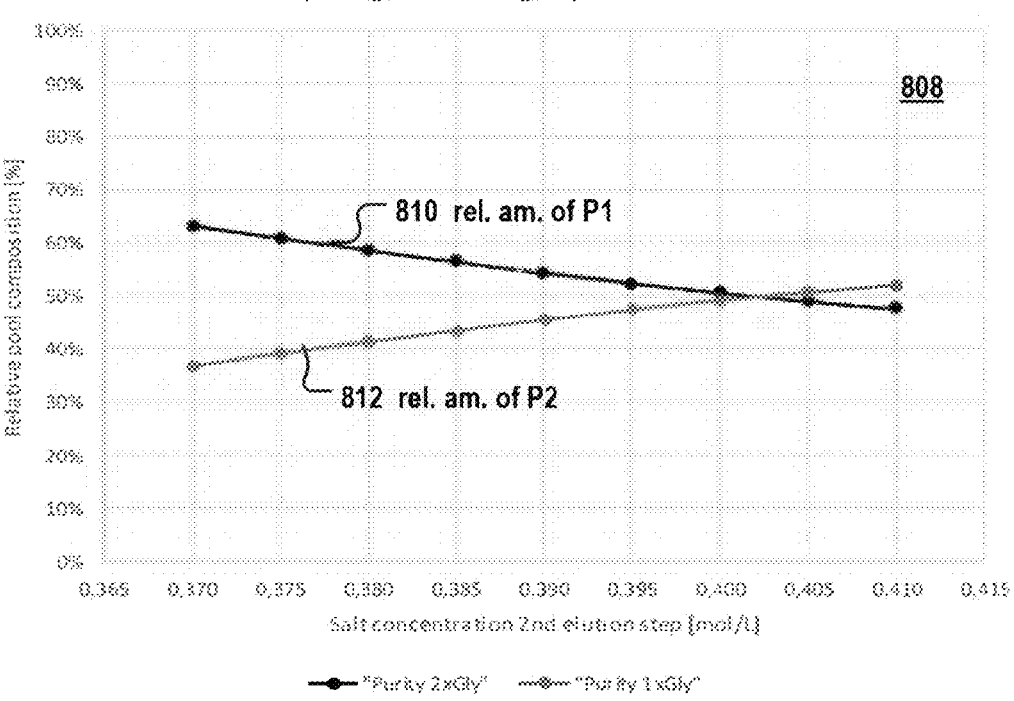
FIG. 8B is a plot illustrating the impact of elution buffer salt concentration on the relative pool composition.

FIG. 8B shows a plot 808 illustrating the impact of the elution buffer salt concentration on the relative protein composition in the elution target volume. Assuming a total protein load of 45 g/L applied on the column, the relative amount of protein P1 in the eluate at different salt concentrations is illustrated in curve 810. The relative amount of protein P2 in the eluate is illustrated in curve 812. Embodiments of the invention allow computationally identifying an elution buffer salt concentration that is specifically adapted to the amount and type of the individual proteins loaded on the column, thereby significantly improving the ability to predict the elution profile of each protein and to collect target elution volumes comprising the desired proteins in the desired amounts and the desired purity.

Empirical tests have shown that the chromatography method according to embodiments of the invention is able to predict desired pool compositions and therefore product qualities which can be important for molecule characterization and the definition of the process design space.

Figure 9:
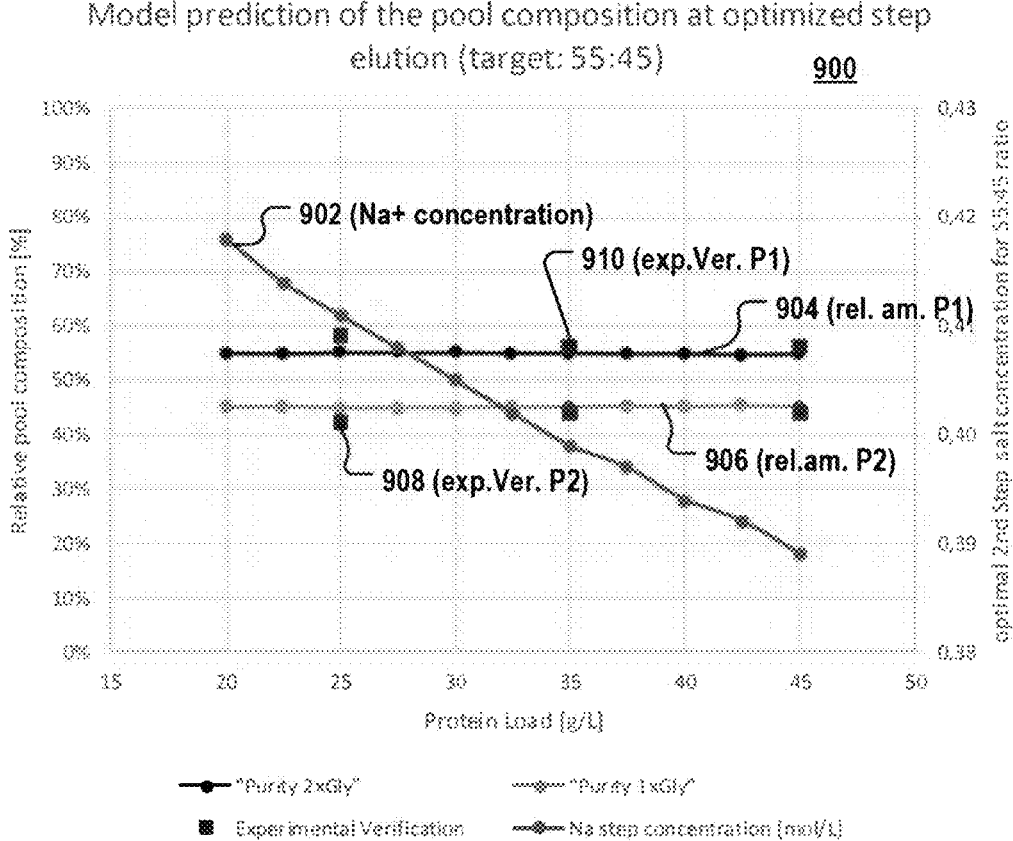
FIG. 9 is a plot illustrating the compensation of the impact of the protein load on the target protein ratio by a predicted elution buffer salt concentration.

FIG. 9 is a plot 900 illustrating the compensation of the impact of the protein load by adapting the elution buffer salt concentration. The chromatography simulation software was used for computationally predicting, for each of a plurality of increasing amounts of protein loaded on the column (x-axis), the elution buffer salt concentration 902 that was able to provide a target elution volume comprising the two target proteins P1, P2 at a desired ratio of 55:45. As can be derived from plot 900, the predicted curves 904, 906 being indicative of the relative amounts of the two target proteins P1, P2 are basically identical to the empirically measured relative amounts 910, 908. The predicted elution salt concentration was able to ensure that irrespective of the protein amounts obtained by preparing the cell culture protein extract and the pre-purification steps (which may vary significantly from case to case), a constant, desired ratio of the two target proteins P1 and P2 were comprised in the target elution volume.

Applicant has observed that simulating and selecting the elution buffer salt concentration in dependence to protein load may significantly increase simulation accuracy and allow identifying a salt concentration that supports an optimization criterion for many types of target proteins. Applicant has observed that both the protein load density and the salt molarity have a strong impact on the elution profile of a protein. By combining this knowledge, the salt concentration can be used as a process steering parameter chosen specifically for individual protein load densities. Optimization of the elution salt molarity in dependence of the protein load density may also allow ensuring a constant product quality.

Figure 10A:
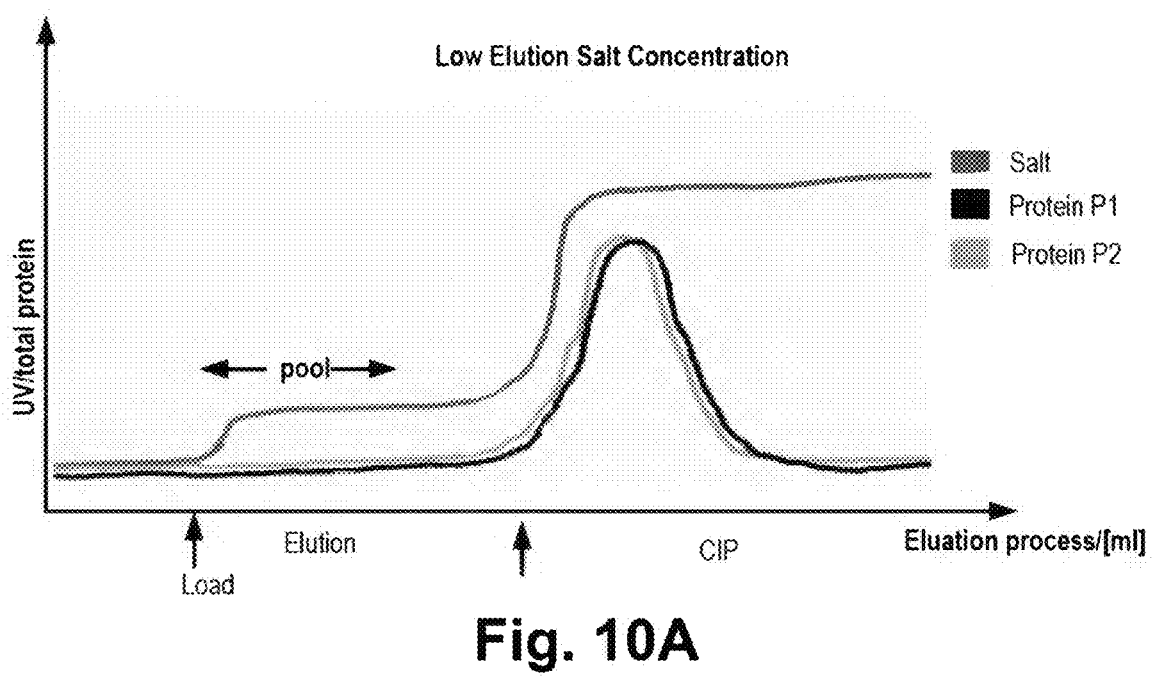
FIGS. 10A-C depict the effect of different salt concentrations on the elution profile of two proteins.
Figure 10B:
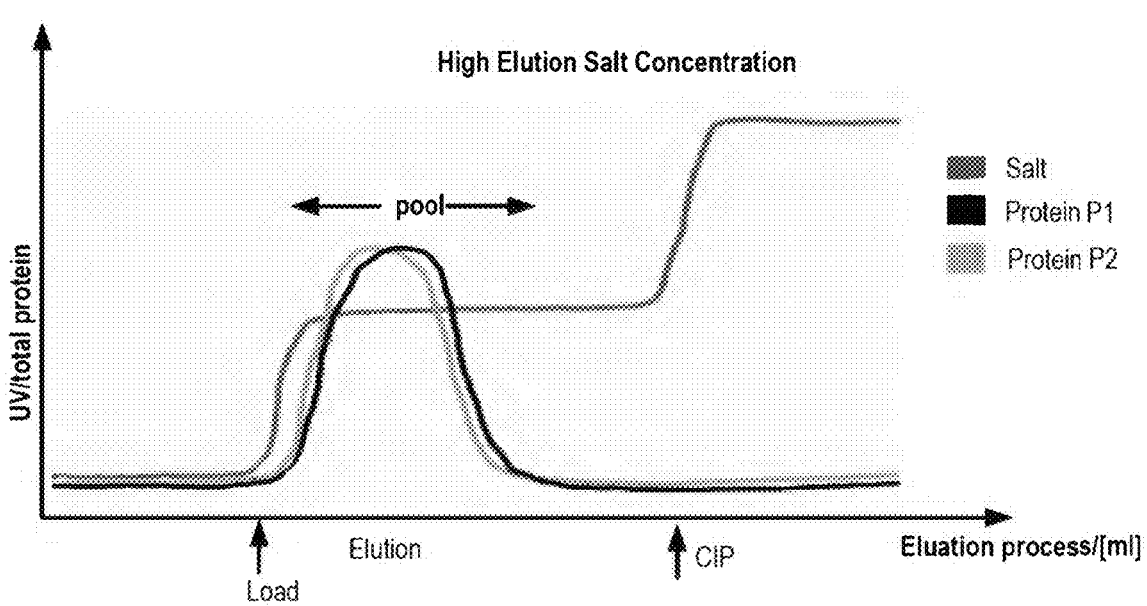
Figure 10C:
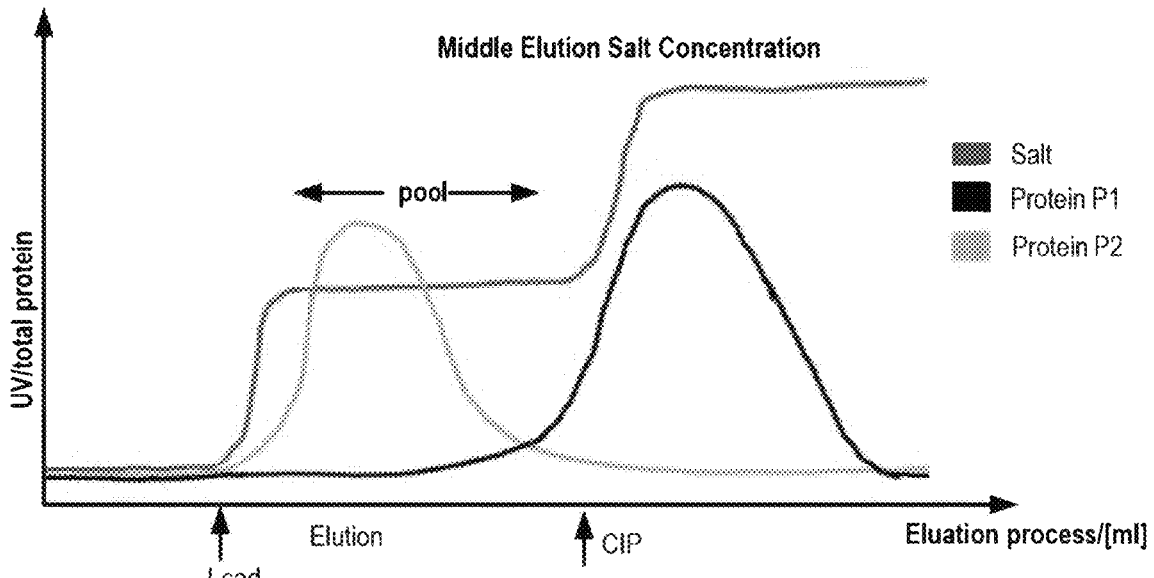

FIGS. 10A-C depicts the effect of the elution buffer salt concentration on the elution profile of two proteins P1, P2.

For example, a first simulation can assume a low elution buffer salt concentration as depicted in FIG. 10A. The elution buffer is not able to separate the proteins P1 and P2 completely or in accordance with a desired protein ratio provided as optimization criterion. Both proteins are eluted in the column cleaning (CIP) step. The eluate obtained in the "pooling" phase is basically free of the proteins P1 and P2.

A second simulation can be based on a high elution buffer salt concentration as depicted in FIG. 10B. This elution buffer is also not possible to separate the two proteins completely or to provide an eluate comprising the two proteins in a desired ratio. The eluate obtained in the pooling phase comprises a large amount of both proteins P1 and P2, but not in the desired ratio (assuming that the desired ratio is other than 1:1).

A third simulation can be based on a medium elution buffer salt concentration as depicted in FIG. 10C. This elution buffer separates the two proteins completely. The eluate obtained in the pooling phase comprises a large amount of protein P1 and is basically free of protein P2.

In case the desired ratio of P1:P2 is e.g. about 1:2, the simulation software can be configured to perform further simulations based on several different elution buffer salt concentrations being lower than the one depicted in FIG. 10B but higher than the one depicted in FIG. 10C to obtain predicted elution profiles for the proteins P1 and P2 and to identify the one of the salt concentrations providing a pooled elution volume whose P1:P2 protein ratio best matches the desired ratio.

The invention claimed is:

1. A chromatography method of producing a target elution volume comprising a first and a second target protein, the method comprising:

providing a cation exchange chromatography column;

applying a protein solution on the column, the protein solution comprising at least the first target protein and the second target protein and optionally one or more further proteins;

inputting an optimization criterion into a chromatography simulation software, the optimization criterion being a desired property of the target elution volume in respect to the first and second target proteins comprised in the target elution volume;

computing, by the chromatography simulation software, an elution buffer salt concentration adapted to elute the first and the second target proteins from the chromatography column such that a target elution volume can be obtained that matches the optimization criterion best, the computation comprising computing a plurality of chromatography simulations as a function of multiple different elution buffer salt concentrations;

computing, by the chromatography simulation software, pooling borders of the target elution volume as a function of at least the computed salt concentration and the input optimization criterion;

applying an elution buffer having the computed salt concentration on the chromatography column;

performing the elution using the applied elution buffer; and collecting the computed target elution volume as a separate fraction using the computed pooling borders, wherein the first and the second target protein are different glycoforms of a monomeric Immunoglobulin G (IgG) Fc-fusion protein of a brain shuttle molecule linked to an immunoglobulin, wherein the brain shuttle molecule a molecule that is able to increase penetration of large molecules such as antibodies into the brain.

2. The chromatography method of claim 1, the optimization criterion being selected from a group comprising:

a) a desired ratio or ratio range of the amounts of the first and of the second target proteins in the target elution volume;

b) a desired amount or amount range of the first target protein in combination with a desired amount or amount range of the second target protein in the target elution volume;

c) a desired purity or purity range of the first target protein in combination with:
a desired ratio of the amounts of the first and second protein in the target elution volume
a desired amount or amount range of the second target protein in the target elution volume;
a desired purity or purity range of the second target protein in the target elution volume; and d) a combination of two or more of the optimization criterion.

3. The chromatography method of claim 1, wherein the applied protein solution comprises the one or more further proteins.

4. The chromatography method of claim 1, wherein the plurality of chromatography simulations are computed as a function of the multiple different elution buffer salt concentrations and as a function of multiple different elution buffer pH values, the method further comprising:

wherein the computing comprises computing a combination of an elution buffer salt concentration and an elution buffer pH value which in combination are adapted to elute the first and the second target proteins from the chromatography column such that a target elution volume can be obtained that matches the optimization criterion best, wherein the chromatography simulations are performed for identifying the combination of the combination of the elution buffer salt concentration and the elution buffer pH;

wherein the pooling borders of the target elution volume are computed as a function of at least the computed combination of the elution buffer salt concentration and the elution buffer pH value and the input optimization criterion; and wherein the elution buffer that is applied on the column has the computed salt concentration and the computed pH value.

5. The method of claim 1, wherein the first and the second target proteins are proteins having a resolution factor of less than 0.75.

6. The method of claim 1, wherein the first and the second target proteins are glycosylation variants of proteins having an identical amino acid sequence.

7. The method of claim 1, wherein the first and the second target proteins are antibody monomers having an identical amino acid sequence and comprising different numbers of glycosyl groups on the FAB fragment.

8. The method of claim 1, wherein the applied protein solution comprises each of the target proteins and each of the further proteins, if any, in a respective concentration of at least 0.5% by weight.

9. The method of claim 1, wherein the second target protein and one or more of the further proteins, if any, comprised in the applied protein solution have an affinity to the stationary phase of the column that is similar as the affinity of the first target protein to the stationary phase leading to overlapping elution behaviors.

10. The method of claim 1, wherein a total amount of protein in the protein solution applied to the column is identical to or smaller than the maximum protein load capacity of the column, and is in a range of 50% to 100% of the maximum protein load capacity.

11. The method of claim 1, wherein the computed pooling borders of the target elution volume are specified in a form of a collection start time offset and a collection stop time offset, the method comprising:

continuously monitoring, by an automated chromatography system comprising the chromatography column, the time lapsed since the starting of the elution;

automatically starting the collecting of the eluted elution buffer by the chromatography system when the lapsed time equals the collection start time offset; and stopping the collecting of the eluted elution buffer by the chromatography system when the lapsed time equals the collection stop time offset.

12. The chromatography method of claim 1, wherein each of the plurality of chromatography simulations is a simulation of a chromatography process using two or more elution steps, whereby in each elution step, an elution buffer with a different elution salt concentration is used, wherein the computed elution buffer salt concentration is a series of different, elusion-step specific elution buffer salt concentrations, and wherein the applying of the elution buffer having the computed salt concentration on the chromatography column comprises step-wise applying a series of elution buffers having the different salt concentrations in accordance with the computed series of elusion-step specific salt concentrations.

13. The chromatography method of claim 1, the method comprising:

inputting an amount of each of the first and second target proteins comprised in the applied protein solution and optionally also the amount of each of one or more further proteins comprised in the applied protein solution, if any, into the chromatography simulation software;

the simulations being computed as a function of a set of parameter values comprising at least:

the dimension of the provided cation exchange chromatography column; and the amounts of the first and second target proteins and optionally also the amounts of the one or more further proteins applied on the column.

14. The chromatography method of claim 13, wherein the set of parameters further comprises:

a predefined pH value of the elution buffer, a flow rate of the elution buffer through the column; and chemical properties of the proteins of the applied protein solution.

15. The method of claim 1, wherein the chromatography simulation software is configured to use a combination of mathematical models for computing the simulations and/or for computing the pooling borders of the target elution volume, the models comprising:

a column model being configured to interrelate the concentration of each of the proteins, the salt concentration and the pH-value in the elution buffer in the interstitial volume of the column; and a pore model being configured to interrelate the concentration of each of the proteins, the salt concentration and the pH value in the elution buffer in the pore volume of the stationary phase of the column; and a reaction model being configured to interrelate the concentration of each of the proteins in the stationary phase, the elution buffer salt concentration and at least some of the chemical properties of each of the proteins in the protein solution.

16. The method of claim 1, wherein the first and the second target protein being different glycoforms of a monomeric Immunoglobulin G (IgG) Fc-fusion protein of a brain shuttle molecule linked to an immunoglobulin, wherein the brain shuttle molecule is a molecule that is able to increase penetration of large molecules such as antibodies into the brain, wherein the fusion protein comprises:

i. an antibody consisting of a full length antibody comprising two pairs each of a full length antibody light chain and a full length antibody heavy chain, and ii. an additional Fab fragment.

17. The method of claim 16, wherein the additional Fab-fragment is the brain shuttle molecule linked to the immunoglobulin.

18. The method of claim 1, wherein the first and the second target protein being different glycoforms of a monomeric Immunoglobulin G (IgG) Fc-fusion protein of a brain shuttle molecule linked to the immunoglobulin, wherein the fusion protein is a bispecific antibody composed of four polypeptides comprising:

one full length antibody comprising two pairs each of a full length antibody light chain and a full length antibody heavy chain, wherein the light chain has a sequence identity to SEQ ID NO: 01 of 70% or more, wherein the heavy chain has a sequence identity to SEQ ID NO: 02 of 70% or more, wherein the binding sites formed by each of the pairs of the full length heavy chain and the full length light chain specifically bind to a first antigen, and one additional Fab fragment having a light chain that has a sequence identity to SEQ ID NO: 03 of 70% or more, and a heavy chain Fab fragment that has a sequence identity to SEQ ID NO: 04 of 70% or more, wherein the additional Fab fragment is fused to the C-terminus of one heavy chain of the full length antibody.

19. The method of claim 18, wherein the light chains of the full length antibody have the amino acid sequence of SEQ ID NO: 01, the first heavy chain of the full length antibody has the amino acid sequence of SEQ ID NO: 02, the light chain of the Fab fragment has the amino acid sequence of SEQ ID NO: 03, and the second heavy chain of the full length antibody fused to the heavy chain of the Fab fragment has the amino acid sequences of SEQ ID NO: 05.

20. A chromatography control system comprising a simulation software, the simulation software being configured for performing a method of obtaining pooling borders of a target elution volume comprising a first and a second target protein, the chromatography control system being configured for:

receiving an optimization criterion and inputting the optimization criterion into the chromatography simulation software, the optimization criterion being a desired property of the target elution volume in respect to the first and second target proteins comprised in the target elution volume;

computing, using the chromatography simulation software, an elution buffer salt concentration adapted to elute the first and the second target proteins from the chromatography column such that a target elution volume can be obtained that matches the optimization criterion best, the computing comprising computing a plurality of chromatography simulations as a function of multiple different elution buffer salt concentrations;

computing the pooling borders of the target elution volume as a function of at least the computed salt concentration and the input optimization criterion; and outputting the computed salt concentration and pooling borders, wherein the first and the second target protein being different glycoforms of a monomeric Immunoglobulin G (IgG) Fc-fusion protein of a brain shuttle molecule linked to an immunoglobulin, and wherein the brain shuttle molecule is a molecule that is able to increase penetration of large molecules such as antibodies into the brain.

21. The chromatography control system of claim 20, the system further being configured for:

receiving dimensions of a cation exchange chromatography column;

receiving the amounts of the first and second target proteins and optionally also the amounts of the one or more further proteins applied on the column;

wherein the simulations and/or the pooling borders are computed as a function of a set of parameter values comprising at least:

the dimension of the provided cation exchange chromatography column; and the amounts of the first and second target proteins and optionally also the amounts of the one or more further proteins applied on the column.

22. The chromatography control system of claim 20, wherein the plurality of chromatography simulations are computed as a function of the multiple different elution buffer salt concentrations and as a function of multiple different elution buffer pH values, the method further comprising:

wherein the computing comprises computing a combination of an elution buffer salt concentration and an elution buffer pH value which in combination are adapted to elute the first and the second target proteins from the chromatography column such that a target elution volume can be obtained that matches the optimization criterion best;

wherein the computing of the pooling borders of the target elution volume is computed as a function of at least the computed combination of the elution buffer salt concentration and the elution buffer pH value and the input optimization criterion; and wherein the computed pH value is output in addition to the computed elution buffer.

23. The chromatography control system of claim 22, wherein the chromatography control system is configured to control a buffer mixing unit as to automatically generate an elution buffer having the output elution salt concentration; and/or the chromatography control system is configured to control a buffer mixing unit as to automatically generate an elution buffer having both the salt concentration and the pH value computed in combination and output according to claim 18; and/or the chromatography control system is configured to control an elution buffer selection unit adapted to automatically select one out of a plurality of available elution buffers having different salt concentrations, the selected elution buffer having the output salt concentration; and/or the chromatography control system is configured to control an elution buffer selection unit adapted to automatically select one out of a plurality of available elution buffers having different salt concentrations and different pH values, the selected elution buffer having both the salt concentration and pH value computed in combination and output according to claim 18; and/or the chromatography control system is configured to control a buffer application unit configured to automatically apply an automatically generated or selected elution buffer on the chromatography column, the applied elution buffer having the output salt concentration or having both the salt concentration and pH value computed in combination and output according to claim 18; or the chromatography control system is configured to control an elution volume collection unit of a chromatography system such that the computed target elution volume is automatically collected as a separate fraction in accordance with the computed pooling borders.

24. A chromatography system comprising the chromatography control system of claim 23, and further comprising the buffer mixing unit and/or the elution buffer selection unit and/or the buffer application unit and/or the automated elution volume collection unit.

25. A non-transitory computer readable medium storing a computer program, which when executed by a computer system, causes the computer system perform a method of managing a chromatography process such that a target elution volume comprising a first and a second target protein is obtained, the computer program comprising a chromatography simulation software and the computer system further configures to perform receiving an optimization criterion being a desired property of a target elution volume in respect to a first and second target proteins comprised in the target elution volume;

computing, using the chromatography simulation software, an elution buffer salt concentration adapted to elute the first and the second target proteins from the chromatography column such that a target elution volume can be obtained that matches the optimization criterion best, the computing comprising computing a plurality of chromatography simulations as a function of multiple different elution buffer salt concentrations;

computing the pooling borders of the target elution volume as a function of at least the computed salt concentration and the input optimization criterion; and outputting the computed salt concentration and/or the pooling borders for enabling a user to control a chromatography system such that a target elution volume comprising the first and the second target proteins in accordance with the optimization criterion is obtained and/or using the computed salt concentration and/or the pooling borders for automatically or semi-automatically controlling a chromatography system such that a target elution volume comprising the first and the second target proteins in accordance with the optimization criterion is obtained, wherein the first and the second target protein being different glycoforms of a monomeric Immunoglobulin G (IgG) Fc-fusion protein of a brain shuttle molecule linked to an immunoglobulin, wherein the brain shuttle molecule is a molecule that is able to increase penetration of large molecules such as antibodies into the brain.

26. The non-transitory computer-readable medium of claim 25, wherein the computer system is further configured for generating control commands for automatically or semi-automatically controlling one or more units of a chromatography system.

*  *  *  *  *

SEQUENCE LISTING

<160> NUMBER OF SEQ ID NOS: 5

<210> SEQ ID NO 1
<211> LENGTH: 215
<212> TYPE: PRT
<213> ORGANISM: Artificial Sequence
<220> FEATURE:
<223> OTHER INFORMATION: 0015-LC1

<400> SEQUENCE: 1

```
Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Thr Tyr Tyr Cys Leu Gln Ile Tyr Asn Met Pro
                85                  90                  95

Ile Thr Phe Gly Gln Gly Thr Lys Val Glu Ile Lys Arg Thr Val Ala
            100                 105                 110

Ala Pro Ser Val Phe Ile Phe Pro Pro Ser Asp Arg Lys Leu Lys Ser
            115                 120                 125

Gly Thr Ala Ser Val Val Cys Leu Leu Asn Asn Phe Tyr Pro Arg Glu
        130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
            165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 2
<211> LENGTH: 455
<212> TYPE: PRT
<213> ORGANISM: Artificial Sequence
<220> FEATURE:
<223> OTHER INFORMATION: 0015-HC1

<400> SEQUENCE: 2

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
            115                 120                 125

Thr Lys Gly Pro Ser Val Phe Pro Leu Ala Pro Ser Ser Lys Ser Thr
        130                 135                 140
```

-continued

```
Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Glu Lys Val
        210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
            275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
                340                 345                 350

Arg Glu Pro Gln Val Cys Thr Leu Pro Pro Ser Arg Asp Glu Leu Thr
            355                 360                 365

Lys Asn Gln Val Ser Leu Ser Cys Ala Val Lys Gly Phe Tyr Pro Ser
        370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Val
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
            435                 440                 445

Ser Leu Ser Leu Ser Pro Gly
    450                 455

<210> SEQ ID NO 3
<211> LENGTH: 215
<212> TYPE: PRT
<213> ORGANISM: Artificial Sequence
<220> FEATURE:
<223> OTHER INFORMATION: 0015-LC2

<400> SEQUENCE: 3

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Ala Trp Tyr Gln Gln Lys Pro Gly Lys Ala Pro Lys Leu Leu Ile
            35                  40                  45
```

-continued

```
Tyr Arg Ala Ser Thr Leu Ala Ser Gly Val Pro Ser Arg Phe Ser Gly
    50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Asn Tyr Ala Ser Ser Asn
                85              90              95

Val Asp Asn Thr Phe Gly Gly Gly Thr Lys Val Glu Ile Lys Ser Ser
            100             105             110

Ala Ser Thr Lys Gly Pro Ser Val Phe Pro Leu Ala Pro Ser Ser Lys
        115             120             125

Ser Thr Ser Gly Gly Thr Ala Ala Leu Gly Cys Leu Val Lys Asp Tyr
    130             135             140

Phe Pro Glu Pro Val Thr Val Ser Trp Asn Ser Gly Ala Leu Thr Ser
145             150             155             160

Gly Val His Thr Phe Pro Ala Val Leu Gln Ser Ser Gly Leu Tyr Ser
                165             170             175

Leu Ser Ser Val Val Thr Val Pro Ser Ser Ser Leu Gly Thr Gln Thr
            180             185             190

Tyr Ile Cys Asn Val Asn His Lys Pro Ser Asn Thr Lys Val Asp Lys
        195             200             205

Lys Val Glu Pro Lys Ser Cys
    210             215
```

<210> SEQ ID NO 4
<211> LENGTH: 229
<212> TYPE: PRT
<213> ORGANISM: Artificial Sequence
<220> FEATURE:
<223> OTHER INFORMATION: 0015-Fab

<400> SEQUENCE: 4

```
Gln Ser Met Gln Glu Ser Gly Pro Gly Leu Val Lys Pro Ser Gln Thr
1               5               10              15

Leu Ser Leu Thr Cys Thr Val Ser Gly Phe Ser Leu Ser Ser Tyr Ala
            20              25              30

Met Ser Trp Ile Arg Gln His Pro Gly Lys Gly Leu Glu Trp Ile Gly
        35              40              45

Tyr Ile Trp Ser Gly Gly Ser Thr Asp Tyr Ala Ser Trp Ala Lys Ser
    50              55              60

Arg Val Thr Ile Ser Lys Thr Ser Thr Thr Val Ser Leu Lys Leu Ser
65              70              75              80

Ser Val Thr Ala Ala Asp Thr Ala Val Tyr Tyr Cys Ala Arg Arg Tyr
                85              90              95

Gly Thr Ser Tyr Pro Asp Tyr Gly Asp Ala Ser Gly Phe Asp Pro Trp
            100             105             110

Gly Gln Gly Thr Leu Val Thr Val Ser Ser Ala Ser Val Ala Ala Pro
        115             120             125

Ser Val Phe Ile Phe Pro Pro Ser Asp Glu Gln Leu Lys Ser Gly Thr
    130             135             140

Ala Ser Val Val Cys Leu Leu Asn Asn Phe Tyr Pro Arg Glu Ala Lys
145             150             155             160

Val Gln Trp Lys Val Asp Asn Ala Leu Gln Ser Gly Asn Ser Gln Glu
                165             170             175

Ser Val Thr Glu Gln Asp Ser Lys Asp Ser Thr Tyr Ser Leu Ser Ser
            180             185             190
```

```
Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 5
<211> LENGTH: 702
<212> TYPE: PRT
<213> ORGANISM: Artificial Sequence
<220> FEATURE:
<223> OTHER INFORMATION: 0015-HC2

<400> SEQUENCE: 5

Gln Val Glu Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Asn Ala Ser Gly Thr Arg Thr Tyr Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Arg Gly Lys Gly Asn Thr His Lys Pro Tyr Gly Tyr Val Arg Tyr
            100                 105                 110

Phe Asp Val Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Glu Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Glu Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320
```

-continued

```
Asp Trp Leu Asn Gly Lys Glu Tyr Lys Cys Lys Val Ser Asn Lys Ala
            325             330             335

Leu Pro Ala Pro Ile Glu Lys Thr Ile Ser Lys Ala Lys Gly Gln Pro
            340             345             350

Arg Glu Pro Gln Val Tyr Thr Leu Pro Pro Cys Arg Asp Glu Leu Thr
            355             360             365

Lys Asn Gln Val Ser Leu Trp Cys Leu Val Lys Gly Phe Tyr Pro Ser
    370             375             380

Asp Ile Ala Val Glu Trp Glu Ser Asn Gly Gln Pro Glu Asn Asn Tyr
385             390             395             400

Lys Thr Thr Pro Pro Val Leu Asp Ser Asp Gly Ser Phe Phe Leu Tyr
            405             410             415

Ser Lys Leu Thr Val Asp Lys Ser Arg Trp Gln Gln Gly Asn Val Phe
            420             425             430

Ser Cys Ser Val Met His Glu Ala Leu His Asn His Tyr Thr Gln Lys
            435             440             445

Ser Leu Ser Leu Ser Pro Gly Gly Gly Ser Gly Gly Gly Gly Ser Gly
    450             455             460

Gly Gly Gly Ser Gly Gly Gly Gly Ser Gln Ser Met Gln Glu Ser Gly
465             470             475             480

Pro Gly Leu Val Lys Pro Ser Gln Thr Leu Ser Leu Thr Cys Thr Val
            485             490             495

Ser Gly Phe Ser Leu Ser Ser Tyr Ala Met Ser Trp Ile Arg Gln His
            500             505             510

Pro Gly Lys Gly Leu Glu Trp Ile Gly Tyr Ile Trp Ser Gly Gly Ser
            515             520             525

Thr Asp Tyr Ala Ser Trp Ala Lys Ser Arg Val Thr Ile Ser Lys Thr
    530             535             540

Ser Thr Thr Val Ser Leu Lys Leu Ser Ser Val Thr Ala Ala Asp Thr
545             550             555             560

Ala Val Tyr Tyr Cys Ala Arg Arg Tyr Gly Thr Ser Tyr Pro Asp Tyr
            565             570             575

Gly Asp Ala Ser Gly Phe Asp Pro Trp Gly Gln Gly Thr Leu Val Thr
            580             585             590

Val Ser Ser Ala Ser Val Ala Ala Pro Ser Val Phe Ile Phe Pro Pro
            595             600             605

Ser Asp Glu Gln Leu Lys Ser Gly Thr Ala Ser Val Val Cys Leu Leu
    610             615             620

Asn Asn Phe Tyr Pro Arg Glu Ala Lys Val Gln Trp Lys Val Asp Asn
625             630             635             640

Ala Leu Gln Ser Gly Asn Ser Gln Glu Ser Val Thr Glu Gln Asp Ser
            645             650             655

Lys Asp Ser Thr Tyr Ser Leu Ser Ser Thr Leu Thr Leu Ser Lys Ala
            660             665             670

Asp Tyr Glu Lys His Lys Val Tyr Ala Cys Glu Val Thr His Gln Gly
            675             680             685

Leu Ser Ser Pro Val Thr Lys Ser Phe Asn Arg Gly Glu Cys
    690             695             700
```